United States Patent
Plettenburg et al.

(10) Patent No.: US 8,524,737 B2
(45) Date of Patent: Sep. 3, 2013

(54) BI- AND POLYCYCLIC SUBSTITUTED ISOQUINOLINE AND ISOQUINOLINONE DERIVATIVES

(75) Inventors: Oliver Plettenburg, Franfurt Am Main (DE); Katrin Lorenz, Frankfurt Am Main (DE); Matthias Loehn, Frankfurt Am Main (DE); Olivier Duclos, Paris (FR); Sandrine Biscarrat, Paris (FR)

(73) Assignee: Sanofi, Paris (FR)

( * ) Notice: Subject to any disclaimer, the term of this patent is extended or adjusted under 35 U.S.C. 154(b) by 122 days.

(21) Appl. No.: 13/000,202

(22) PCT Filed: Jun. 18, 2009

(86) PCT No.: PCT/EP2009/004393
§ 371 (c)(1),
(2), (4) Date: Apr. 19, 2011

(87) PCT Pub. No.: WO2009/156092
PCT Pub. Date: Dec. 30, 2009

(65) Prior Publication Data
US 2011/0190340 A1  Aug. 4, 2011

Related U.S. Application Data

(60) Provisional application No. 61/153,155, filed on Feb. 17, 2009.

(30) Foreign Application Priority Data

Jun. 24, 2008  (EP) .................... 08290607

(51) Int. Cl.
C07D 495/08 (2006.01)
C07D 217/24 (2006.01)
A61K 31/47 (2006.01)

(52) U.S. Cl.
USPC ........................... 514/309; 546/141

(58) Field of Classification Search
None
See application file for complete search history.

(56) References Cited

U.S. PATENT DOCUMENTS

| | | | |
|---|---|---|---|
| 5,480,883 A | 1/1996 | Spada et al. |
| 6,903,107 B1 | 6/2005 | Timmers et al. |
| 7,217,722 B2 | 5/2007 | Takami et al. |
| 7,618,985 B2 | 11/2009 | Ray et al. |
| 2003/0220368 A1 | 11/2003 | Ozaki et al. |
| 2004/0138286 A1 | 7/2004 | Imazaki et al. |
| 2006/0079556 A1 | 4/2006 | Sher et al. |
| 2007/0060595 A1 | 3/2007 | Yoshizawa et al. |
| 2008/0045566 A1 | 2/2008 | Ray et al. |
| 2008/0242699 A1 | 10/2008 | Plettenburg et al. |
| 2009/0088429 A1 | 4/2009 | Plettenburg et al. |
| 2009/0093518 A1 | 4/2009 | Plettenburg et al. |
| 2010/0056518 A1 | 3/2010 | Plettenburg et al. |
| 2010/0056553 A1 | 3/2010 | Plettenburg et al. |
| 2010/0056566 A1 | 3/2010 | Plettenburg et al. |
| 2010/0056568 A1 | 3/2010 | Plettenburg et al. |
| 2010/0063025 A1 | 3/2010 | Plettenburg et al. |
| 2010/0081671 A1 | 4/2010 | Plettenburg et al. |
| 2010/0105650 A1 | 4/2010 | Plettenburg et al. |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 A | 4/1998 |
| WO | 9202476 | 2/1992 |
| WO | 9706802 | 2/1997 |
| WO | 9723214 | 7/1997 |
| WO | WO98/06433 | 2/1998 |
| WO | 9911642 | 3/1999 |
| WO | 0024718 | 5/2000 |
| WO | 0073299 | 12/2000 |
| WO | WO01/39726 A2 | 6/2001 |
| WO | 0153288 | 7/2001 |
| WO | 0156988 | 8/2001 |
| WO | 0164656 | 9/2001 |
| WO | WO 01/64238 A2 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |

(Continued)

OTHER PUBLICATIONS

Alvarez, M. et al., "Product Class 5: Isoquinolines," Science of Synthesis (2005), vol. 15, pp. 661-838.
Alvarez, M. et al., "Product Class 6: Isoquinolines,"Science of Synthesis (2005), vol. 15, pp. 839-906.
Ai, Shingo et al., "Rho-Rho kinase is involved in smooth muscle cell migration through myosin light chain phosphorylation-dependent and independent pathways," Atherosclerosis (2001), vol. 155, pp. 321-327.

(Continued)

*Primary Examiner* — Zinna Northington Davis
(74) *Attorney, Agent, or Firm* — Scully, Scott, Murphy & Presser, P.C.

(57) ABSTRACT

The invention relates to bi- and polycyclic substituted isoquinoline and isoquinolinones of the formula (I) wherein $R_1$ to $R_{12}$ are as defined in the application useful for the treatment and/or prevention of diseases associated with Rho-kinase and/or Rho-kinase mediated phosphorylation of myosin light chain phosphatase, and compositions containing such compounds.

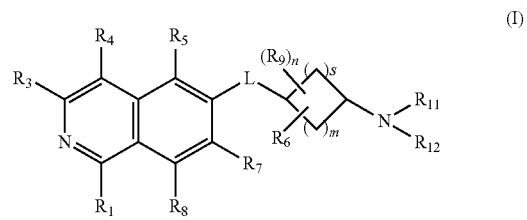

37 Claims, No Drawings

(56) References Cited

FOREIGN PATENT DOCUMENTS

| | | |
|---|---|---|
| WO | 02088101 | 11/2002 |
| WO | 03018556 | 3/2003 |
| WO | 03024450 | 3/2003 |
| WO | WO03/053330 A2 | 7/2003 |
| WO | 2004113297 | 12/2004 |
| WO | WO2004/106325 A1 | 12/2004 |
| WO | 2005035933 | 2/2005 |
| WO | 2005035516 | 4/2005 |
| WO | WO2005/030130 A2 | 4/2005 |
| WO | WO2005/030791 A2 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | WO2007/012421 A1 | 2/2007 |
| WO | WO2007/012422 A1 | 2/2007 |
| WO | WO2007/039563 A1 | 4/2007 |
| WO | 2007065916 | 6/2007 |
| WO | 2008020081 | 2/2008 |
| WO | WO2008/020081 A1 | 2/2008 |
| WO | WO2008/077555 A2 | 7/2008 |
| WO | WO2008/077556 A1 | 7/2008 |

OTHER PUBLICATIONS

Bauer, Markus et al., "Dichotomous Regulation of Myosin Phoshorylation and Shape Change by Rho-Kinase and Calcium in Intact Human Platelets," Blood (1999), vol. 94, pp. 1665-1672.
Chellaiah, Meenakshi et al., "Rho-dependent Rho Kinase Activation Increases CD44 Surface Expression and Bone Resorption in Osteoclasts," The Journal of Biological Chemistry (2003), vol. 278, pp. 29086-29097.
Chitaley, Kanchan et al., "Antagonism of Rho-kinase stimulates rat penile erection via a nitric oxide-independent pathway," Nature Medicine (2001), vol. 7, pp. 119-122.
Maruoka, Shuichiro et al., "Elastase Anti-elastase imbalance in the Pathogens of COPD," Nippon Rinsho (1999), vol. 57, pp. 1982-1987.
Demiryürek, Seniz et al., "Effects of fasudil, a Rho-kinase inhibitor, on myocardial preconditioning in anesthetized rats," European Journal of Pharmacology (2005), vol. 527, pp. 129-140.
Retzer, Michaela et al., "Mildly oxidised low density lipoprotein induces platelet shape change via Rho-kinase-dependent phosphorylation of myosin light chain and moesin," FEBS Letters (2000), vol. 466, pp. 70-74.
Kimura, Kazushi et al., "Regulation of the Association of Adducin with Actin Filaments by Rho-associated Kinase (Rho-kinase) and Myosin Phosphatase," The Journal of Biological Chemistry (1998), vol. 273, pp. 5542-5548.
Fukumoto, Y. et al., "Acute vasodilator effects of a Rho-kinase inhibitor, fasudil, in patients with severe pulmonary hypertension," Heart (2005), vol. 91, pp. 391-392.
Gingras, Denis et al., "Tyrosine phosphorylation of the vascular endothelial-growth-factor receptor-2 (VEGFR-2) is modulated by Rho proteins," Biochemical Journal (2000), vol. 348, pp. 273-280.
Gokina, Natalia I. et al., "Effects of Rho kinase inhibition on cerebral artery myogenictone and reactivity," Journal of Applied Physiology (2005), vol. 98, pp. 1940-1948.
Yoshida, Yoshiki et al., "Studies on Anti-*Helicobacter pylori* Agents. Part 1: Benzyloxyisoquinoline Derivatives," Bioorganic and Medicinal Chemistry (1999), vol. 7, pp. 2647-2666.
Hara, Masahito et al., "Protein kinase inhibition by fasudil hydrochloride promotes neurological recovery after spinal cord injury in rats," Journal of Neurosurgery: Spine 1(2000), vol. 93, pp. 94-101.
Hattori, Tsuyoshi et al., "Long-Term Inhibition of Rho-Kinase Suppresses Left Ventricular Remodeling After Myocardial Infarction in Mice," Circulation (2004), vol. 109, pp. 2234-2239.
Hitomi, Asako et al., "Hemorheological abnormalities in experimental cerebral ischemia and effects of protein kinase inhibitor on blood fluidity," Life Sciences (2000), vol. 67, pp. 1929-1939.
Honjo, Megumi et al., "Effects of Rho-Associated Protein Kinase Inhibitor Y-27632 on Intraocular Pressure and Outflow Facility," Investigative Ophthalmology and Visual Science (2001), vol. 42, pp. 137-144.
Inoue, Makoto et al., "Initiation of neuropathic pain requires lysophosphatidic acid receptor signaling," Nature Medicine (2004), vol. 10, pp. 712-718.
Itoh, Kazuyuki et al., "An essential part for Rho-associated kinase in the transcellular invasion of tumor cells," Nature Medicine (1999), vol. 5, pp. 221-225.
Kawaguchi, Atsuhiro et al., "The effect of a Rho kinase inhibitor Y-27632 on superoxide production, aggregation and adhesion in human polymorphonuclear leukocytes," European Journal of Pharmacology (2000), vol. 403, pp. 203-208.
Kim, Inkyeom et al., "Thin and Thick Filament Regulation of Contractility in Experimental Cerebral Vasospasm," Neurosurgery (2000), vol. 46, pp. 440-447.
Amano, Mutsuki et al., "Formation of Actin Stress Fibers and Focal Adhesions Enhanced by Rho-Kinase," Science (1997), vol. 275, pp. 1308-1311.
Kishi, Takuya et al., "Rho-Kinase Inhibitor Improves Increased Vascular Resistance and Impaired Vasodilation of the Forearm in Patients with Heart Failure," Circulation (2005), vol. 111, pp. 2741-2747.
Klages, Birgit et al., "Activation of $G_{12}/G_{13}$ Results in Shape Change and Rho/Rho-Kinase-mediated Myosin Light Chain Phosphorylation in Mouse Platelets," The Journal of Cell Biology (1999), vol. 144, pp. 745-754.
Noma, Kensuke et al., "Physiological role of ROCKs in the cardiovascular systems," American Journal of Physiology: Cell Physiology (2006), vol. 290, pp. C661-C668.
Lin, Tong et al., "Rho-ROCK-LIMK-Cofilin Pathway Regulates Shear Stress Activation of Sterol Regulatory Element Binding Proteins," Circulation Research (2003), vol. 92, pp. 1296-1304.
Furukawa, Noboru et al., "Role of Rho-kinase in regulation of insulin action and glucose homeostasis," Cell Metabolism (2005), vol. 2, pp. 119-129.
Masumoto, Akihiro et al., "Suppression of Coronary Artery Spasm by the Rho-Kinase Inhibitor Fasudil in Patients With Vasospastic Angina," Circulation (2002), vol. 105, pp. 1545-1547.
Nakahara, Tsutomu et al., "Y-27632 potentiates relaxant effects of $\beta_2$—adrenoceptor agonists in bovine tracheal smooth muscle," European Journal of Pharmacology (2000), vol. 389, pp. 103-106.
Pacaud, P. et al., "Rho proteins and vascular diseases," Archives des Maladies du Coeur et des Vaisseaux (2005), vol. 98, pp. 249-254.
Pommereau, Antje et al., "Two Simple and Generic Antibody-Independent Kinase Assays: Comparison of a Bioluminescent and a Microfluidic Assay Format," Journal of Biomedical Screening (2004), vol. 9, pp. 409-416.
Remington's Pharmaceutical Sciences 17th Edition (1985), p. 1418.
Retzer, Michaela et al., "Lysophosphatidic acid-induced platelet shape change proceeds via Rho/Rho kinase-mediated myosin light-chain and moesin phosphorylation," Cellular Signalling (2000), vol. 12, pp. 645-648.
Vicente-Manzanares, Miguel et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis," The Journal of Immunology (2002), vol. 168, pp. 400-410.
Vicente-Manzanares, Miguel et al., "The RhoA Effector mDia is Induced During T Cell Activation and Regulates Actin Polymerization and Cell Migration in T Lymphocytes," The Journal of Immunology (2003), vol. 171, pp. 1023-1034.
Sandu, Oana A. et al., "Diabetes in the Goto-Kakizaki Rat is Accompanied by Impaired Insulin-Mediated Myosin-Bound Phosphatase Activation and Vascular Smooth Muscle Cell Relaxation," Diabetes (2000), vol. 49, pp. 2178-2189.
Sato, Motohiko et al., "Involvement of Rho-Kinase-Mediated Phosphorylation of Myosin Light Chain in Enhancement of Cerebral Vasospasm," Circulation Research (2000), vol. 87, pp. 195-200.
Satoh, Shin-Ichi et al., "Pharmacological profile of hydroxy fasudil as a selective rho kinase inhibitor on ischemic brain damage," Life Sciences (2001), vol. 69, pp. 1441-1453.
Setoguchi, Hidekazu et al., "Leukotriene $C_4$ enhances the contraction of porcine tracheal smooth muscle through the activation of Y-27632, a rho kinase inhibitor, sensitive pathway," British Journal of Pharmacology (2001), vol. 132, pp. 111-118.

Shimokawa, Hiroaki et al., "Anti-anginal Effect of Fasudil, a Rho-Kinase Inhibitor, in Patients With Stable Effort Angina: A Multicenter Study," Journal of Cardiovascular Pharmacology (2002), vol. 40, pp. 751-761.

Steioff, Kerstin et al., "Long term Rho-kinase inhibition ameliorates endothelial dysfunction in LDL-Receptor deficient mice," European Journal of Pharmacology (2005), vol. 512, pp. 247-249.

Seasholtz, Tammy M. et al., "Rho and Rho Kinase Mediate Thrombin-Stimulated Vascular Smooth Muscle Cell DNA Synthesis and Migration," Circulation Research (1999), vol. 84, pp. 1186-1193.

Tatsumi, S. et al., "Involvement of Rho-Kinase in Inflammatory and Neuropathic Pain Through Phosphorylation of Myristoylated Alanine-Rich C-Kinase Substrate (Marcks)," Neuroscience (2005), vol. 131, pp. 491-498.

Forzato, Cristina et al., "Baker's yeast reduction of 4-hetero-2-(2-nitroethyl)cyclohexanones," Tetrahedron: Asymmetry (1997), vol. 8, pp. 1811-1820.

Uehata, Masayoshi et al., "Calcium sensitization of smooth muscle mediated by a Rho-associated protein kinase in hypertension," Nature (1997), vol. 389, pp. 990-994.

Yamakawa, Tadashi et al., "Involvement of Rho-Kinase in Angiotensin II-Induced Hypertrophy of Rat Vascular Smooth Muscle Cells," Hypertension (2000), vol. 35, pp. 313-318.

Yamamoto, Yasuhiro et al., "The Protein Kinase inhibitor Fasudil Protects Against Ischemic Myocardial Injury Induced by Endothelin-1 in the Rabbit," Journal of Cardiovascular Pharmacology (2000), vol. 35, pp. 203-211.

Totsukawa, Go et al., "Distinct Roles of ROCK (Rho-kinase) and MLCK in Spatial Regulation of MLC Phosphorylation for Assembly of Stress Fibers and Focal Adhesions in 3T3 Fibroblasts," The Journal of Cell Biology (2000), vol. 150, pp. 797-806.

Yoshii, Akihiro et al., "Relaxation of Contracted Rabbit Tracheal and Human Bronchial Smooth Muscle by Y-27632 through Inhibition of $Ca^{2+}$Sensitization," American Journal of Respiratory Cell and Molecular Biology (1999), vol. 20, pp. 1190-1200.

Zhou, Yan et al., "Nonsteroidal Anti-Inflammatory Drugs Can Lower Amyloidogenic $A\beta_{42}$ by Inhibiting Rho," Science (2003), vol. 302, pp. 1215-1217.

Okada, Hiroshi et al., "Synthesis and Antitumor Activities of Prodrugs of Benzoylphenylureas," Chemical and Pharmaceutical Bulletin (1994), vol. 42, pp. 57-61.

Negoro, Nobuyuki et al., "The Kinase Inhibitor Fasudil (HA-1077) Reduces Intimal Hyperplasia through Inhibiting Migration and Enhancing Cell Loss of Vascular Smooth Muscle Cells," Biochemical and Biophysical Research Communications (1999), vol. 262, pp. 211-215.

Somlyo, Avril V. et al., "Rho-Kinase Inhibitor Retards Migration and in Vivo Dissemination of Human Prostate Cancer Cells," Biochemical and Biophysical Research Communications (2000), vol. 269, pp. 652-659.

Uchida, Shigeki et al., "The Suppression of Small GTPase Rho Signal Transduction Pathway Inhibits Angiogenesis in Vitro and in Vivo," Biochemical and Biophysical Research Communications (2000), vol. 269, pp. 633-640.

Wakino, Shu et al., "Rho/Rho Kinase as a Potential Target for the Treatment of Renal Disease," Drug News and Perspectives (2005), vol. 18, pp. 639-643.

Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.

Takami, A. et al., "Design and Synthesis of Rho Kinase Inhibitors (I)" Bioorganic & Medicinal Chemistry (2004) pp. 2115-2137, vol. 12.

Iwakubo, M. et al., "Design and Synthesis of Rho Kinase Inhibitors (III)" Bioorganic & Medicinal Chemistry (2007) pp. 1022-1033, vol. 15.

Iwakubo, M. et al., "Design and Synthesis of Rho Kinase Inhibitors (II)" Bioorganic & Medicinal Chemistry (2007) pp. 350-364, vol. 15.

Tamura, M. et al., "Development of Specific Rho-Kinase Inhibitors and Their Clinical Application" Biochimicia et Biophysica Acta (2005) pp. 245-252, vol. 1754.

Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.

Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.

Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.

Caron, S. et al., "The Synthesis of a Selective PDE4/TNFα Inhibitor" Organic Process Research and Development (2001) pp. 587-592, vol. 5.

U.S. Appl. No. 12/970,376, filed Dec. 16, 2010, Inventor: Plettenburg, et al, entitled: "6-Substituted Isoquinolines and Isoquinolinones".

U.S. Appl. No. 13/000,754, filed Apr. 20, 2011, Inventor: Plettenburg et al., entitled: "Substituted Isoquinolines and Isoquinolinones as Rho Kinase Inhibitors".

Curran, T.T. et al., "The Preparation of Optically Active 2-Cyclopenten-1,4-Diol Derivatives from Furfurl Alcohol" Tetrahedron, pp. 1983-2004, vol. 53(6), Feb. 10, 1997.

BI- AND POLYCYCLIC SUBSTITUTED ISOQUINOLINE AND ISOQUINOLINONE DERIVATIVES

CONTINUING DATA

This application is a 371 of PCT/EP2009/004393 filed Jun. 18, 2009 which claims the benefit of U.S. Provisional Application No. 61/153,155 filed on Feb. 17, 2009.

The present invention relates to bi- and polycyclic substituted isoquinoline and isoquinolinone derivatives, their preparation, pharmaceutical preparations containing these derivatives and their use in the treatment and/or prevention of diseases related to the inhibition of Rho-kinase and/or of Rho-kinase mediated phosphorylation of myosin light chain phosphatase.

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al. Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-1948), bronchial smooth muscle contraction (Yoshii et al. Am. J. Resp. Cell Mol. Biol. 1999, 20, 1190-1200), asthma (Setoguchi et al. Br. J. Pharmacol. 2001, 132, 111-118; Nakahara et al. Eur. J. Pharmac. 2000, 389, 103-106) and chronic obstructive pulmonary disease (COPD, Maruoka et al. Nippon Rinsho, 1999, 57, 1982-1987), hypertension, pulmonary hypertension (Fukumoto et al. Heart 2005, 91, 391-392, Mukai et al. Nature 1997, 389, 990-994) and ocular hypertension and regulation of intraoccular pressure (Honjo et al. Invest. Ophthalmol. Visual Sci. 2001, 42, 137-144), endothelial dysfunction (Steioff et al. Eur. J. Pharmacol. 2005, 512, 247-249), angina (Masumoto et al. Circulation 2002, 105, 1545-47, Shimokawa et al. J. Cardiovasc. Pharmacol. 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-643), myocardial infarction (Demiryurek et al. Eur. J. Pharmacol. 2005, 527, 129-140, Hattori et al. Circulation 2004, 109, 2234-2239), cardiac hypertrophy and failure (Yamakawa et al. Hypertension 2000, 35, 313-318; Liao et al. Am. J. Physiol. Cell Physiol. 2006, 290, C661-668; Kishi et al. Circulation 2005, 111, 2741-2747), coronary heart disease, artherosclerosis, restenosis (Pacaud et al. Arch. Mal. Coeur 2005, 98, 249-254; Retzer et al. FEBS Lett. 2000, 466, 70-74; Negoro et al. Biochem. Biophys. Res. Commun. 1999, 262, 211-215), diabetes, diabetic complications, glucose utilization and metabolic syndrome (Sandu et al. Diabetes 2000, 49, 2178-2189; Maeda et al. Cell Metab. 2005, 2, 119-129), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Nara et al. J. Neurosurg. 2000, 93, 94-101), cerebral ischemia (Uehara et al. Nature 1997, 389, 990-994; Satoh et al. Life Sci. 2001, 69, 1441-1453; Hitomi et al. Life Sci. 2000, 67, 1929-1939; Yamamoto et al. J. Cardiovasc. Pharmacol. 2000, 35, 203-211), cerebral vasospasm (Sato et al. Circ. Res. 2000, 87, 195-200; Kim et al. Neurosurgery 2000, 46, 440-447), pain, e.g. neuropathic pain (Tatsumi et al. Neuroscience 2005, 131, 491-498; Inoue et al. Nature medicine 2004, 10, 712-718), infection of digestive tracts with bacteria (WO 98/06433), cancer development and progression, neoplasia where inhibition of Rho kinase has been shown to inhibit tumor cell growth and metastasis (Itoh et al. Nature Medicine 1999, 5, 221-225; Somlyo et al. Biochem. Biophys. Res. Commun. 2000, 269, 652-659), angiogenesis (Uchida et al. Biochem. Biophys. Res. Commun. 2000, 269, 633-640; Gingras et al. Biochem. J. 2000, 348, 273-280), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa et al. FEBS Lett. 2000, 466, 70-74; Bauer et al. Blood 1999, 94, 1665-1672; Klages et al. J. Cell Biol. 1999, 144, 745-754; Retzer et al. Cell Signal 2000, 12, 645-648) and leukocyte aggregation (Kawaguchi et al. Eur. J. Pharmacol. 2000, 403, 203-208; Sanchez-Madrid et al. J. Immunol. 2003, 171, 1023-1034; Sanchez-Madrid, et al. J. Immunol. 2002, 168, 400-410), and bone resorption (Chellaiah et al. J. Biol. Chem. 2003, 278, 29086-29097). Na/H exchange transport system activation (Kawaguchi et al. Eur. J. Pharmacol. 2000, 403, 203-208), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res. 2003, 92, 1296-304).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 2001/64238 describes isoquinoline-5-sulfonamide derivatives optionally substituted by a —$(CH_2)_{1-6}$—O—

$(CH_2)_{0-6}$—, a —$(CH_2)_{0-6}$—S—$(CH_2)_{0-6}$— or a —$(CH_2)_{0-6}$-linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—$(C_0-C_{10})$alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[$(C_1-C_6)$alkylene)]$_{0-1}$-Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I—X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO2003/053330 (Ube) generically describes isoquinolone derivatives of the formula

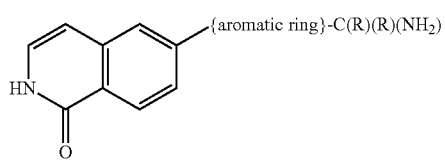

as Rho-kinase inhibitors.

WO2007/012422 (Sanofi-Aventis) generically describes isoquinoline and isoquinolone derivatives of the formula

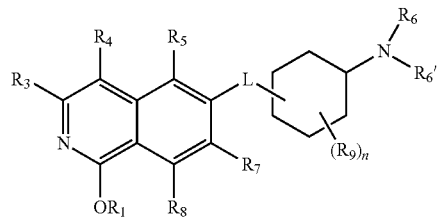

as Rho-Kinase inhibitors.

WO2008/077555 and WO 2008/077556 (sanofi-aventis) also describe 6 substituted isoquinoline and isoquinolone derivatives as Rho-kinase inhibitors.

WO2007/039563 and WO 2008/020081 (Organon) describe 6-substituted isoquinoline derivatives as Rho-kinase inhibitors.

Although several Rho-kinase inhibitors have been described there still remains the need for additional compounds useful in the treatment of Rho-kinase mediated diseases.

An embodiment of the present invention is a compound of the formula (I)

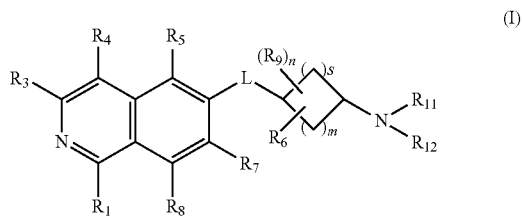

wherein $R_1$ is H, OH or $NH_2$;

$R_3$ is H, halogen, CN, $(C_1-C_6)$alkyl, OH, $NH_2$, or NHR';

$R_4$ is H, halogen, hydroxy, CN, $(C_1-C_6)$alkyl, R', or $(C_1-C_6)$alkylene-R';

$R_5$ is H, halogen, CN, $(C_1-C_6)$alkyl, or R';

$R_7$ is H, halogen, CN, $(C_1-C_6)$alkyl, O—$(C_1-C_6)$alkyl, R', or $SO_2$—$NH_2$;

$R_8$ is H, halogen or $(C_1-C_6)$alkyl;

$R_6$ is one $(C_1-C_4)$alkylene bound to the cycloalkyl ring, in which the $(C_1-C_4)$alkylene forms a second bond to a different carbon atom of the cycloalkyl ring to form a bicyclic ring system, wherein in the bicyclic ring system one or two carbon atoms are replaced by a group independently selected from O, N—$R_{13}$, S, SO or $SO_2$;

or, if m and s are 2, m is 3 and s is 1, or m is 4 and s is 0, $R_6$ is $CH_2$—CH—$(CH_2)_2$ which is bound with one $CH_2$ to the cycloalkyl ring and the two other $CH_2$ are bound to different carbon atoms of the cycloalkyl ring, and, if m is 3 and s is 3, $R_6$ are two methylene groups bound to different carbon atoms of the cycloalkyl ring, wherein the methylene groups or the $CH_2$—CH—$(CH_2)_2$ group are bound to carbon atoms of the cycloalkyl ring and form an adamantane system of the formula

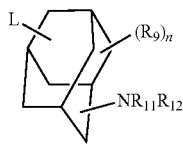

(XX)

wherein L can be bound to any secondary or tertiary carbon atom, or $R_6$ together with $R_{11}$ and the N atom form a $(C_3-C_8)$ heterocycloalkyl which is fused or connected as a spirocyclic ring system to the cycloalkyl residue to form a residue of the formula

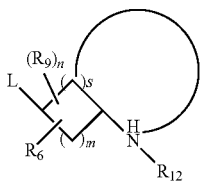

(XXI)

wherein the bicyclic ring system or adamantane system or the $(C_3-C_8)$heterocycloalkyl containing ring system is unsubstituted or optionally substituted by $R_9$;

$R_9$ is
R',
OH,
halogen,
$(C_1-C_6)$alkyl,
O—$(C_1-C_6)$alkyl,
$(C_1-C_6)$alkylene-R',
$(C_2-C_6)$alkenyl,
$(C_2-C_6)$alkynyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
COOH,
C(O)O—$(C_1-C_6)$alkyl,
C(O)OR'
C(O)$(C_1-C_6)$alkyl,
C(O)R',
CONH$_2$,
C(O)—NH—$(C_2-C_6)$alkenyl,
C(O)—NH—$(C_2-C_6)$alkynyl,
C(O)NH—$(C_1-C_6)$alkyl,
C(O)NHR',
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R', or
C(O)O$(C_1-C_6)$alkylene-R';
$R_{11}$ and $R_{12}$ are independently of each other
H,
R',
$(C_1-C_6)$alkyl,
$(C_1-C_6)$alkylene-R',
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$,
$(C_1-C_6)$alkylene-C(O)O—$(C_1-C_6)$alkyl,
C(O)O—$(C_1-C_6)$alkyl,
C(O)OR',
C(O)$(C_1-C_6)$alkyl,
C(O)R',
C(O)NH—$(C_1-C_6)$alkyl,
C(O)NHR',
C(O)N[$(C_1-C_6)$alkyl]R'
C(O)N[$(C_1-C_6)$alkyl]$_2$,
C(O)—$(C_1-C_6)$alkylene-R',
C(O)O$(C_1-C_6)$alkylene-R', or
$R_{11}$ and $R_{12}$, together with the N-atom to which they are attached, form a $(C_3-C_8)$ heterocycloalkyl;
$R_{13}$ is H or $(C_1-C_6)$alkyl;
n is 0, 1, 2, 3 or 4;
m is 1, 2, 3 or 4;
s is 0, 1, 2, or 3;
L is O(CH$_2$)$_p$, S(CH$_2$)$_p$, S(O)(CH$_2$)$_p$, SO$_2$(CH$_2$)$_p$, NH(CH$_2$)$_p$, N($C_1-C_6$)alkyl-(CH$_2$)$_p$, N($C_3-C_6$)cycloalkyl-(CH$_2$)$_p$; or N[($C_1-C_3$)alkylene-R']-(CH$_2$)$_p$;
p is 0, 1, 2, 3 or 4;
R' is
$(C_3-C_8)$cycloalkyl,
$(C_5-C_{10})$heteroaryl,
$(C_3-C_8)$heterocycloalkyl,
$(C_6-C_{10})$aryl;
wherein in residues $R_3$ to $R_{13}$ alkyl or alkylene is unsubstituted or optionally substituted one or more times by OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{13}$ cycloalkyl or heterocloalkyl is unsubstituted or optionally substituted one or more times by $(C_1-C_6)$alkyl, halogen, OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{13}$ alkyl or alkylene is unsubstituted or optionally substituted one or more times by halogen;
wherein in residues $R_3$ to $R_{13}$ $(C_6-C_{10})$aryl and $(C_5-C_{10})$heteroaryl are unsubstituted or optionally substituted one or more times by a group independently selected from halogen, OH, NO$_2$, N$_3$, CN, C(O)—$(C_1-C_6)$alkyl, C(O)—$(C_6-C_{10})$aryl, C(O)OH, C(O)O$(C_1-C_6)$alkyl, C(O)NH$_2$, C(O)NH$(C_1-C_6)$alkyl, C(O)N[$(C_1-C_6)$alkyl]$_2$, $(C_3-C_8)$cycloalkyl, $(C_1-C_6)$alkyl, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, PO$_3$H$_2$, SO$_3$H, SO$_2$—NH$_2$, SO$_2$NH$(C_1-C_6)$alkyl, SO$_2$N[$(C_1-C_6)$alkyl]$_2$, S—$(C_1-C_6)$alkyl; SO—$(C_1-C_6)$alkyl, SO$_2$—$(C_1-C_6)$alkyl, SO$_2$—N=CH—N[$(C_1-C_6)$alkyl]$_2$, SF$_5$,
C(NH)(NH$_2$), NH$_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—SO$_2$—$(C_1-C_6)$alkyl, NH—SO$_2$—$(C_6-C_{10})$aryl, NH—SO$_2$—$(C_5-C_{10})$heteroaryl, NH—SO$_2$—$(C_3-C_8)$heterocycloalkyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$ aryl, $(C_5-C_{10})$heteroaryl, $(C_3-C_8)$heterocycloalkyl, $(C_1-C_6)$alkylene-$(C_5-C_{10})$heteroaryl, $(C_1-C_6)$alkylene-$(C_3-C_8)$heterocycloalkyl, O—$(C_1-C_6)$alkylene-$(C_5-C_{10})$heteroaryl, O—$(C_1-C_6)$alkylene-$(C_3-C_8)$heterocycloalkyl, wherein the $(C_6-C_{10})$aryl, $(C_5-C_{10})$heteroaryl, $(C_3-C_8)$heterocycloalkyl, or $(C_3-C_8)$cycloalkyl may be substituted one to three times by a group independently selected from halogen, OH, $NO_2$, CN, O—$(C_1-C_6)$alkyl, $(C_1-C_6)$alkyl, $NH_2$, NH$(C_1-C_6)$alkyl, N[$(C_1-C_6)$alkyl]$_2$, $SO_2CH_3$, C(O)OH, C(O)O—$(C_1-C_6)$alkyl, C(O)$NH_2$, $(C_1-C_6)$alkylene-O—$(C_1-C_6)$alkyl, $(C_1-C_6)$alkylene-O—$(C_6-C_{10})$aryl, or O—$(C_1-C_6)$alkylene-$(C_6-C_{10})$aryl;

or wherein $(C_6-C_{10})$aryl is vicinally substituted by a O—$(C_1-C_4)$alkylene-O group whereby a 5-8-membered ring is formed together with the carbon atoms the oxygen atoms are attached to;

and wherein aryl substituents of $(C_6-C_{10})$aryl, $(C_5-C_{10})$heteroaryl, $(C_3-C_8)$heterocycloalkyl and $(C_3-C_8)$cycloalkyl groups may not be further substituted by an aryl, heteroaryl, heterocycloalkyl or cycloalkyl containing group;

their stereoisomeric and/or tautomeric forms and/or their pharmaceutically acceptable salts thereof.

In another embodiment the present invention also relates to a compound of formula (I) and/or its pharmaceutically acceptable salt for use as a medicament. It also relates to the use of at least one compound of formula (I) and/or a pharmaceutically acceptable salt thereof for the treatment and/or prevention of Rho-Kinase mediated diseases such as hypertension, pulmonary hypertension, ocular hypertension, retinopathy, glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy, infection of digestive tracts with bacteria, sepsis or cancer development and progression. The invention further relates to a medicament comprising an effective amount of at least one compound of formula (I) and/or a pharmacologically acceptable salt thereof. Another object of the present invention is a method of producing a compound of formula (I).

The term alkyl as used in $(C_1-C_2)$alkyl, $(C_1-C_4)$alkyl, or $(C_1-C_6)$alkyl and the corresponding alkylene substituents are understood as a hydrocarbon residue which can be linear, i.e. straight-chain, or branched and has 1, 2, 3, 4, 5, or 6 carbon atoms, respectively. This also applies if an alkyl group occurs as a substituent on another group, for example in an alkoxy group (O-alkyl), S-alkyl or a —O$(C_1-C_6)$alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may optionally be halogenated once or more, e.g. alkyl groups may be fluorinated, e.g. perfluorinated. Examples of halogenated alkyl groups are $CH_2F$, $CHF_2$, $CF_3$ and $CH_2CF_3$, $OCF_3$, $SCF_3$, or —O—$(CF_2)_2$—O—.

The term $(C_2-C_6)$-alkenyl means a hydrocarbon residue whose carbon chain is straight-chain or branched and comprises 2 to 6 carbon atoms and has, depending on the chain length, 1, 2 or 3 double bonds, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. The double bond may where possible have the E or Z orientation. The double bonds may be both internal and terminal.

$(C_2-C_6)$-alkynyl groups are hydrocarbon residue whose carbon chain is straight-chain or branched and comprises 2 to 6 carbon atoms and have, depending on the chain length, 1 or 2 triple bonds, for example, ethynyl, 1-propynyl, 2-propynyl (=propargyl) or 2-butynyl. The triple bonds may be both internal and terminal.

Halogen means fluoro (F), chloro (Cl), bromo (Br) or iodo (I).

The term $(C_1-C_8)$heteroalkyl or the corresponding $(C_1-C_8)$heteroalkylene substituents are understood as $(C_1-C_8)$alkyl or $(C_1-C_8)$alkylene groups wherein at least one carbon atom, preferably one or two carbon atoms, more preferred one carbon atom, is replaced by a group selected from O, NH, or S and wherein the nitrogen and sulfur atoms may optionally be oxidized. The heteroatom may be placed at any position of the alkyl or alkylene group. Examples of $(C_1-C_8)$heteroalkyl groups include —$CH_2$—O—$CH_3$, —$CH_2$—$CH_2$—O—$CH_2$—$CH_3$, —$CH_2$—NH—$CH_2$—$CH_3$, —$CH_2$—N($CH_2$—$CH_3$)$_2$—$CH_2$—$CH_2$—$CH_2$—O—$CH_3$, —$CH_2$—$CH_2$—$CH_2$—S—$CH_3$, —$CH_2$—O—CH($CH_3$)$_2$, —$CH_2$—O—$CH_2$—$CH_2$—O—$CH_3$ or O—$CH_2$—$CH_3$.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl, which can be bonded via any carbon atom.

A $(C_6-C_{10})$aryl group means an aromatic ring or a ring system which comprises two aromatic rings which are fused or otherwise linked or which comprises two fused aromatic rings wherein one ring is saturated or partly saturated, i.e contains at least one C—C single bond, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

$(C_3-C_8)$heterocycloalkyl group means a saturated (contains no double bonds) monocyclic carbon ring system containing 3, 4, 5, 6, 7 or 8 ring atoms in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocycloalkyl residues can be bound at any positions, for example on the 1-position, 2-position, 3-position, 4-position, 5-position, 6-position, 7-position or 8-position. Also included are the corresponding N-oxides, sulfoxides or sulfones of these compounds.

Examples of $(C_3-C_8)$heterocycloalkyl groups are oxiranyl, oxetanyl, aziridinyl, tetrahydrofuranyl, tetrahydropyranyl, dioxolanyl, for example 1,3-dioxolanyl, dioxanyl, for example 1,4-dioxanyl, piperidinyl, pyrrolidinyl, imidazolidinyl, triazolidinyl, hexahydropyrimidinyl, piperazinyl, triazinanyl, for example, 1,3,5-triazinanyl, 1,2,3-triazinanyl or 1,2,4-triazinanyl, tetrahydrothiophenyl, tetrahydro-thiopyranyl, dithiolanyl, for example 1,3-dithiolanyl, dithianyl, thiazolidinyl, oxazolidinyl, oxathiolanyl, for example 1,3-oxathiolanyl, morpholinyl or thiomorpholinyl, diazepanyl, for example 1,4-diazepanyl.

A preferred ($C_3$-$C_8$)heterocycloalkyl group is morpholinyl, pyrrolidinyl, piperazinyl, piperidinyl, oxetanyl or tetrahydropyranyl.

($C_5$-$C_{10}$)heteroaryl means a mono- or bicyclic ring system in which one or more carbon atoms can be replaced by one or more heteroatoms such as, for example 1, 2, 3 or 4 nitrogen atoms, 1 or 2 oxygen atoms, 1 or 2 sulfur atoms or combinations of different hetero atoms. The heteroaryl residues can be bound at any position, for example on the 1-position, 2-position, 3-position, 4-position, 5-position, 6-position, 7-position or 8-position. ($C_5$-$C_{10}$)heteroaryl groups may be an (1) aromatic monocyclic or bicyclic ring system or (2) a bicyclic ring system wherein one ring is aromatic and the second ring is at least partially saturated.

Also included are the corresponding N-oxides, sulfoxides or sulfones of these compounds.

Suitable ($C_5$-$C_{10}$)heteroaryl groups are benzimidazolyl, benzofuryl, benzothienyl, azaindolyl, benzothiophenyl, benzoxazolyl, benzthiazolyl, benztriazolyl, benzisoxazolyl, benzisothiazolyl, carbolinyl, cinnolinyl, chromanyl, chromenyl, naphthyridinyl, phthalazinyl, pyridoimidazolyl, pteridinyl, purynyl, quinazolinyl, quinoxalinyl, quinolinyl, isoquinolinyl, tetrahydroisoquinolinyl, tetrahydroquinolinyl, indolinyl, indolizinyl, indolyl, furyl, furazanyl, thienyl, imidazolyl, imidazolinyl, 1H-indazolyl, pyrazolyl, oxazolyl, 1,2,3-oxadiazolyl, 1,2,4-oxadiazolyl, 1,2,5-oxadiazolyl, 1,3,4-oxadiazolyl, isoxazolyl, thiazolyl, isothiazolyl, pyridyl, triazolyl, pyrazinyl, pyrimidinyl, pyridazinyl, pyrazolinyl, pyrrolyl, 1,2,3-thiadiazolyl, 1,2,4-thiadiazolyl, 1,2,5-thiadiazolyl, 1,3,4-thiadiazolyl, tetrazolyl.

Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in ($C_5$-$C_{10}$)heteroaryl residues can occur on free carbon atoms or on nitrogen atoms.

Preferred examples of ($C_5$-$C_{10}$)heteroaryl residues are benzofuryl, quinolinyl, furyl, thienyl, imidazolyl, pyrazolyl, oxazolyl, isoxazolyl, thiazolyl, isothiazolyl, pyridyl, triazolyl, oxadiazolyl, pyrazinyl, pyrimidinyl, pyridazinyl and tetrazolyl.

A preferred ($C_5$-$C_{10}$)heteroaryl is a ($C_5$-$C_6$)heteroaryl group. Preferred ($C_5$-$C_6$)heteroaryl residues are furyl, thienyl, imidazolyl, pyrazolyl, oxazolyl, isoxazolyl, thiazolyl, isothiazolyl, pyridyl, triazolyl, oxadiazolyl, pyrazinyl, pyrimidinyl, and pyridazinyl. Preferred examples of ($C_5$-$C_6$)heteroaryl residues are 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2- or -5-yl, 2-, 4- or 5-thiazolyl, 3-, 4- or 5-isothiazolyl, 2-, 3- or 4-pyridyl, 2-, 4-, 5- or 6-pyrimidinyl, 3- or 4-pyridazinyl, or pyrazinyl.

In residues $R_3$ to $R_{13}$ ($C_6$-$C_{10}$)aryl and ($C_5$-$C_{10}$)heteroaryl residues are unsubstituted or, if not specified otherwise, optionally substituted one or more times, preferably one to three times, by a group independently selected from halogen, OH, $NO_2$, $N_3$, CN, C(O)—($C_1$-$C_6$)alkyl, C(O)—($C_6$-$C_{10}$)aryl, C(O)OH, C(O)O($C_1$-$C_6$)alkyl, C(O)$NH_2$, C(O)NH($C_1$-$C_6$)alkyl, C(O)N[($C_1$-$C_6$)alkyl]$_2$, ($C_3$-$C_8$)cycloalkyl, ($C_1$-$C_6$)alkyl, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, $PO_3H_2$, $SO_3H$, $SO_2$—$NH_2$, $SO_2NH$($C_1$-$C_6$)alkyl, $SO_2N$[($C_1$-$C_6$)alkyl]$_2$, S—($C_1$-$C_6$)alkyl; SO—($C_1$-$C_6$)alkyl, $SO_2$—($C_1$-$C_6$)alkyl, $SO_2$—N=CH—N[($C_1$-$C_6$)alkyl]$_2$, $SF_5$, C(NH)($NH_2$), $NH_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—$SO_2$—($C_1$-$C_6$)alkyl, NH—$SO_2$—($C_6$-$C_{10}$)aryl, NH—$SO_2$—($C_5$-$C_{10}$)heteroaryl, NH—$SO_2$—($C_3$-$C_8$)heterocycloalkyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heteroaryl, ($C_3$-$C_8$)heterocycloalkyl, ($C_1$-$C_6$)alkylene-($C_5$-$C_{10}$)heteroaryl, ($C_1$-$C_6$)alkylene-($C_3$-$C_5$)heterocycloalkyl, O—($C_1$-$C_6$)alkylene-($C_5$-$C_{10}$)heteroaryl, O—($C_1$-$C_6$)alkylene-($C_3$-$C_8$)heterocycloalkyl;

wherein said ($C_6$-$C_{10}$)aryl or ($C_5$-$C_{10}$)heteroaryl, ($C_3$-$C_8$)heterocycloalkyl or ($C_3$-$C_8$)cycloalkyl may be substituted one to three times by a group independently selected from halogen, OH, $NO_2$, CN, O—($C_1$-$C_6$)alkyl, ($C_1$-$C_6$)alkyl, $NH_2$, NH($C_1$-$C_6$)alkyl, N[($C_1$-$C_6$)alkyl]$_2$, $SO_2CH_3$, C(O)OH, C(O)O—($C_1$-$C_6$)alkyl, C(O)$NH_2$, ($C_1$-$C_6$)alkylene-O—($C_1$-$C_6$)alkyl, ($C_1$-$C_6$)alkylene-O—($C_6$-$C_{10}$)aryl, or O—($C_1$-$C_6$)alkylene-($C_6$-$C_{10}$)aryl;

or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to;

and wherein aryl substituents of ($C_6$-$C_{10}$)aryl, ($C_5$-$C_{10}$)heteroaryl, ($C_3$-$C_8$)heterocycloalkyl or ($C_3$-$C_8$)cycloalkyl groups may not be further substituted by an aryl, heteroaryl, heterocycloalkyl or cycloalkyl containing group.

Preferred substituents for ($C_6$-$C_{10}$)aryl and ($C_5$-$C_{10}$)heteroaryl groups are OH, ($C_1$-$C_4$)alkyl, O—($C_1$-$C_4$)alkyl, O-phenyl, phenyl, C(O)O—($C_1$-$C_6$)alkyl, C(O)OH, C(O)—($C_1$-$C_4$)alkyl, halogen, $NO_2$, $SO_2NH_2$, CN, $SO_2$—($C_1$-$C_4$)alkyl, $SO_2$—N=CH—N[($C_1$-$C_6$)alkyl]$_2$, NH—$SO_2$—($C_1$-$C_4$)alkyl, $NH_2$, NH—C(O)—($C_1$-$C_4$)alkyl, ($C_3$-$C_8$)cycloalkyl, ($C_1$-$C_4$)alkyl-OH, C(O)N[($C_1$-$C_4$)alkyl]$_2$, CONH($C_1$-$C_6$)alkyl, C(O)$NH_2$, N[($C_1$-$C_4$)alkyl]$_2$, ($C_1$-$C_4$)alkylene-N[($C_1$-$C_4$)alkyl]$_2$, ($C_1$-$C_4$)alkylene-O—($C_1$-$C_4$)alkyl, ($C_5$-$C_6$)heteroaryl, ($C_3$-$C_8$)heterocycloalkyl, ($C_1$-$C_4$)alkylene-($C_6$-$C_{10}$)aryl, wherein the ($C_6$-$C_{10}$)aryl may be further substituted one to three times, preferably once, by halogen, ($C_1$-$C_4$)alkyl, O—($C_1$-$C_4$)alkyl, ($C_1$-$C_4$)alkylene-O—($C_1$-$C_6$)alkyl, ($C_6$-$C_{10}$)aryl, O—($C_1$-$C_6$)alkylene-($C_6$-$C_{10}$)aryl, or may be vicinally substituted by a O—($C_1$-$C_4$)alkylene-O group whereby a 5-8-membered ring is formed together with the carbon atoms the oxygen atoms are attached to.

More preferred substituents for ($C_6$-$C_{10}$)aryl and ($C_5$-$C_{10}$)heteroaryl are OH, halogen, CN, phenyl, O-phenyl, NH—C(O)—($C_1$-$C_4$)alkyl, C(O)—($C_1$-$C_4$)alkyl, C(O)—O($C_1$-$C_4$)alkyl, ($C_1$-$C_4$)alkyl, O—($C_1$-$C_4$)alkyl, $CONH_2$, $SO_2$—$NH_2$, $SO_2$—($C_1$-$C_4$)alkyl or $SO_2$—N=CH—N[($C_1$-$C_4$)alkyl]$_2$, ($C_1$-$C_4$)alkylene-phenyl, ($C_1$-$C_4$)alkylene-O—($C_1$-$C_4$)alkyl or ($C_5$-$C_6$)heteroaryl, wherein the phenyl is unsubstituted or optionally substituted one to three times, preferably once, by OH, halogen, ($C_1$-$C_4$)alkyl or O—($C_1$-$C_4$)alkyl.

Even more preferred substituents for ($C_6$-$C_{10}$)aryl and ($C_5$-$C_{10}$)heteroaryl are OH, halogen, CN, phenyl, O-phenyl, NH—C(O)—($C_1$-$C_4$)alkyl especially NH—C(O)—$CH_3$, C(O)—($C_1$-$C_4$)alkyl especially C(O)—$CH_3$, C(O)—O($C_1$-$C_4$)alkyl especially C(O)—$OCH_3$, ($C_1$-$C_4$)alkyl especially $CH_3$ or $CF_3$, O—($C_1$-$C_4$)alkyl especially O—$CH_3$, $CONH_2$, $SO_2$—$NH_2$, $SO_2$—($C_1$-$C_4$)alkyl especially $SO_2$—$CH_3$ or $SO_2$—$CF_3$; or $SO_2$—N=CH—N[($C_1$-$C_4$)alkyl]$_2$ especially $SO_2$—N=CH—N[($CH_3$)$_2$, wherein the phenyl is unsubstituted or optionally substituted one to three times, preferably once, by OH, halogen, ($C_1$-$C_4$)alkyl or O—($C_1$-$C_4$)alkyl.

More especially preferred substituents for $(C_6-C_{10})$aryl and $(C_5-C_{10})$heteroaryl groups are OH, CN, $(C_1-C_4)$alkyl especially $CH_3$ or $CF_3$, $O(C_1-C_4)$alkyl especially $O$—$CH_3$, halogen or phenyl, wherein the phenyl may be further substituted one to three times, preferably once, by OH, halogen, $(C_1-C_4)$alkyl especially $CH_3$ or $CF_3$, or $O$—$(C_1-C_4)$alkyl especially $O$—$CH_3$.

Most preferred substituents for $(C_6-C_{10})$aryl and $(C_5-C_{10})$heteroaryl groups are OH, CN, halogen, $(C_1-C_4)$alkyl especially $CH_3$ or $CF_3$, $O(C_1-C_4)$alkyl especially $O$—$CH_3$, or halogen.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

In residues $R_3$ to $R_{13}$ an alkyl or alkylene is unsubstituted or, if not specified otherwise, optionally substituted one or more times by halogen. If substituted, alkyl or alkylene is preferably substituted one to three times by halogen selected from chloro or bromo but may be substituted by fluoro once or more, e.g. being perfluorinated. Preferably halogen is fluoro. Preferably alkylene is not halogenated. More preferred an alkyl or alkylene is not halogenated.

In residues $R_3$ to $R_{13}$ alkyl or alkylene is unsubstituted or, if not specified otherwise, optionally substituted one or more times by a group selected independently from OH, $OCH_3$, COOH, $COOCH_3$, $NH_2$, $NHCH_3$, $N(CH_3)_2$, $CONH_2$, $CONHCH_3$ or $CON(CH_3)_2$. If substituted, the number of substituents is preferably between 1, 2, 3 or 4, more preferably 1 or 2 with 1 being even more preferred. Preferably an alkylene is not substituted by one of these groups. More preferably an alkyl or alkylene is not substituted by one of these groups. Preferably alkyl or alkylene in $R_3$, $R_4$, $R_5$, $R_7$ and $R_8$ are not substituted. In a further embodiment alkyl or alkylene in $R_4$, $R_5$, $R_7$ and $R_8$ to $R_{14}$ is not substituted by one of these groups.

In residues $R_3$ to $R_{13}$ cycloalkyl or heterocycloalkyl is unsubstituted or, if not specified otherwise, optionally substituted one or more times by $(C_1-C_6)$alkyl, halogen, OH, $OCH_3$, COOH, $COOCH_3$, $NH_2$, $NHCH_3$, $N(CH_3)_2$, $CONH_2$, $CONHCH_3$ or $CON(CH_3)_2$.

If substituted, the number of substituents is preferably between 1, 2, 3 or 4, more preferably 1 or 2 with 1 being even more preferred. Preferably cycloalkyl or heterocycloalkyl in $R_3$, $R_4$, $R_5$, $R_7$ and $R_9$ are not substituted. In a further embodiment cycloalkyl or heterocycloalkyl in $R_3$ to $R_{13}$ is not substituted. In a preferred embodiment a heterocycloalkyl is not substituted. In another embodiment cycloalkyl is not substituted.

The general and preferred substituents of $(C_6-C_{10})$aryl, $(C_5-C_{10})$heteroaryl, $(C_3-C_8)$heterocycloalkyl and $(C_3-C_8)$cycloalkyl groups as defined before may be combined with the general and preferred definitions of $R_1$, $R_3$, $R_4$, $R_5$, $R_6$, $R_7$, $R_8$, $R_9$, $R_{11}$, $R_{12}$, $R_{13}$, n, s, m, p and L as described in the following embodiments of a compound of formula (I).

The following embodiments of a compound of formula (I) do further characterize and are part of the present invention.

In one embodiment of a compound of formula (I) $R_1$ is H and the compound is characterized by the formula (II)

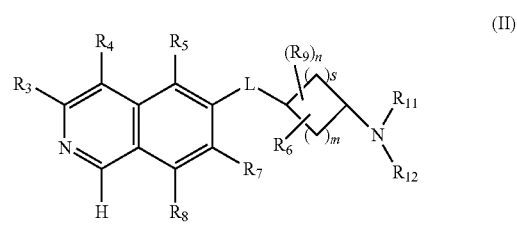

(II)

In another embodiment of the present invention $R_1$ is OH and the compound is characterized by the formula (IIIa)

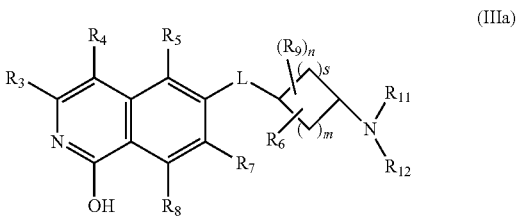

(IIIa)

The isoquinoline derivative of formula (I), wherein $R_1$ is OH, includes the corresponding tautomeric 1-isoquinolone derivative which is characterized by the formula (IIIb)

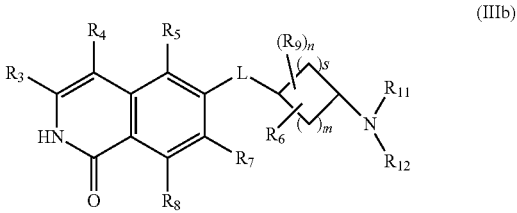

(IIIb)

This tautomeric form is also an embodiment of the present invention.

In a further embodiment $R_1$ is $NH_2$ and the compound is characterized by the formula (IV)

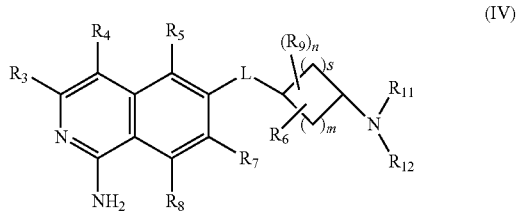

(IV)

The following further embodiments equally refer to the compounds of formula (I), (II), (IIIa), (IIIb) and (IV).

In a preferred embodiment $R_1$ is H or OH; more preferably $R_1$ is OH.

In one embodiment $R_3$ is preferably H, halogen, $(C_1-C_6)$alkyl, or NH—R'. In another more preferred embodiment $R_3$ is H, halogen, unsubstituted or substituted NH—($C_5$-$C_6$)heteroaryl, unsubstituted or substituted NH—($C_3$-$C_8$)heterocycloalkyl or unsubstituted or substituted NH-phenyl. In a even more preferred embodiment $R_3$ is unsubstituted or substituted NH—($C_5$-$C_6$)heteroaryl containing one or more N atoms, or unsubstituted or substituted NH-phenyl. In a most preferred embodiment $R_3$ is H. Examples of NHR' substituents in $R_3$ are

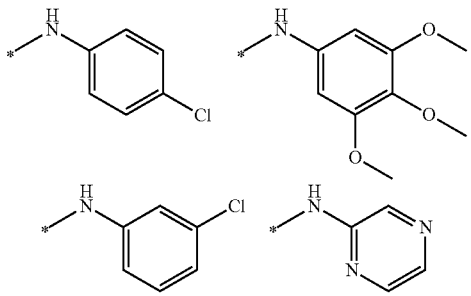

The asterisk (*) denotes where the bond is connected to the C-atom of the ring.

In a preferred embodiment $R_4$ is H, halogen, ($C_1$-$C_6$)alkyl, or ($C_1$-$C_2$)-phenyl. In a more preferred embodiment $R_4$ is H, halogen or unsubstituted or substituted ($C_1$-$C_4$)alkyl or ($C_1$-$C_2$)-phenyl, preferably unsubstituted ($C_1$-$C_4$)alkyl or ($C_1$-$C_2$)-phenyl. Most preferred $R_4$ is H.

In a preferred embodiment $R_5$ is H, CN, halogen, unsubstituted or substituted ($C_1$-$C_6$)alkyl, unsubstituted or substituted ($C_6$-$C_{10}$)aryl, or unsubstituted or substituted ($C_5$-$C_{10}$)heteroaryl. Examples of $R_5$ are hydrogen, fluoro, chloro, bromo, iodo, methyl, ethyl, phenyl, thienyl or pyridyl, nitrile, (p-methoxy)-phenyl, N-aniline, cyclopropyl, tetrazol, 4-methoxy-aniline. In a more preferred embodiment ($C_1$-$C_6$)alkyl, ($C_6$-$C_{10}$)aryl or ($C_5$-$C_{10}$)heteroaryl are unsubstituted. In an even more preferred embodiment $R_5$ is H, halogen, methyl, ethyl, phenyl, thienyl, or pyridyl, more specifically H, halogen, methyl, or ethyl. Most preferred $R_5$ is H.

In a preferred embodiment $R_7$ is H, halogen, nitrile, unsubstituted or substituted ($C_1$-$C_6$)alkyl, unsubstituted or substituted O—($C_1$-$C_6$)alkyl, or unsubstituted or substituted R'. In a more preferred embodiment $R_7$ is H, halogen, nitrile, unsubstituted or substituted ($C_1$-$C_4$)alkyl, unsubstituted or substituted O—($C_1$-$C_4$)alkyl, unsubstituted or substituted phenyl, unsubstituted or substituted ($C_5$-$C_6$)heteroaryl, or unsubstituted or substituted ($C_3$-$C_6$)cycloalkyl. Preferably, ($C_1$-$C_6$) alkyl, phenyl or ($C_5$-$C_6$)heteroaryl are unsubstituted.

In an even more preferred embodiment $R_7$ is H, fluoro, chloro, bromo, methyl, ethyl, methoxy, phenyl, nitrile, cyclopropyl, or thienyl. More preferably $R_7$ is H, fluoro, chloro, bromo, methyl or methoxy, in particular H or chloro. Most preferred $R_7$ is chloro.

In a preferred embodiment $R_8$ is H, Cl, F, methyl or ethyl. In a more preferred embodiment $R_8$ is H.

In a preferred embodiment $R_9$ is R', OH, halogen, ($C_1$-$C_6$)alkyl, ($C_1$-$C_6$)alkylene-R', ($C_2$-$C_6$)alkenyl, ($C_1$-$C_6$)alkylene-C(O)NH—R', ($C_1$-$C_6$)alkylene-C(O)NH—($C_1$-$C_6$)alkyl, COOH, CONH$_2$, C(O)NH—($C_1$-$C_6$)alkyl, C(O)NHR', C(O)—NH—($C_1$-$C_6$)alkynyl, C(O)—NH($C_1$-$C_6$)alkylene-R', or C(O)N[($C_1$-$C_6$)alkyl]$_2$; wherein alkyl, alkylene and R' are unsubstituted or substituted.

In a more preferred embodiment $R_9$ is OH, halogen, ($C_1$-$C_6$)alkyl, R', ($C_1$-$C_6$)alkylene-R', ($C_2$-$C_6$)alkenyl, COOH, CONH$_2$, C(O)NH—($C_1$-$C_6$)alkyl, C(O)NHR', or C(O)N[($C_1$-$C_6$)alkyl]$_2$, wherein alkyl, alkylene and R' are unsubstituted or substituted.

More preferably $R_9$ is OH, halogen, ($C_1$-$C_6$)alkyl, ($C_2$-$C_6$)alkenyl, COOH, CONH$_2$, O—CH$_3$, phenyl, ($C_5$-$C_6$)heteroaryl, ($C_3$-$C_8$)heterocycloalkyl, ($C_1$-$C_2$)alkylene-phenyl, ($C_3$-$C_8$)cycloalkyl, wherein alkyl, phenyl, ($C_3$-$C_5$)cycloalkyl, ($C_5$-$C_6$)heteroaryl or ($C_3$-$C_8$)heterocycloalkyl is unsubstituted or substituted. Even more preferred $R_9$ is OH, halogen, ($C_1$-$C_6$)alkyl, COON, CONH$_2$, O—CH$_3$, phenyl, ($C_1$-$C_2$)alkylene-phenyl, ($C_3$-$C_8$)cycloalkyl, wherein alkyl, phenyl or ($C_3$-$C_5$)cycloalkyl is unsubstituted or substituted.

Most preferred $R_9$ is allyl, methyl, ethyl, propyl, isopropyl, butyl, isobutyl, cyclopropyl, cyclobutyl, cyclopentyl, cyclopropylmethylene, isopropyloxymethylene, tetrahydrofuranyl, tetrahydropyranyl, phenyl or benzyl.

$R_9$ may be bound to any carbon atom of the ring including the position where the linker group L is bound.

As examples for these embodiments, $R_9$ is methyl, ethyl, propyl, isopropyl, phenyl,

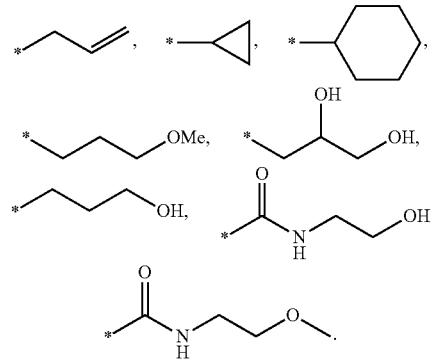

The asterisk (*) denotes where the bond is connected to the C-atom of the ring.

In one embodiment of a compound of formula (I) $R_{11}$ and $R_{12}$ are independently of each other
H,
R',
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R',
C(O)NH—($C_1$-$C_6$)alkyl,
C(O)NHR',
C(O)N[($C_1$-$C_6$)alkyl]$_2$, wherein
R', ($C_1$-$C_6$)alkyl and ($C_1$-$C_6$)alkylene are unsubstituted or substituted.

In a preferred embodiment of a compound of formula (I) $R_{11}$ and $R_{12}$ are independently of each other
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
($C_1$-$C_4$)alkylene-($C_6$-$C_{10}$)aryl,
($C_1$-$C_4$)alkylene-O—($C_1$-$C_6$)alkyl,
C(O)NH—($C_1$-$C_6$)alkyl, or
$R_{11}$ and $R_{12}$, together with the N-atom to which they are attached, form a ($C_3$-$C_8$) heterocycloalkyl group,
wherein ($C_1$-$C_6$)alkyl, ($C_3$-$C_8$)cycloalkyl, ($C_1$-$C_4$)alkylene, ($C_5$-$C_{10}$)heteroaryl, ($C_3$-$C_8$)heterocycloalkyl, ($C_6$-$C_{10}$)aryl are unsubstituted or substituted.

Preferably the formed heterocyclyl group in $R_{11}$ and $R_{12}$ is morpholinyl, piperidinyl, pyrrolidinyl or piperazinyl. More preferably the heterocyclyl group is morpholinyl or piperazinyl.

In a more preferred embodiment of a compound of formula (I) $R_{11}$ is H, $(C_1-C_6)$alkyl, $(C_3-C_8)$cycloalkyl, or $(C_1-C_4)$alkylene-$(C_3-C_8)$cycloalkyl; and
$R_{12}$ is
H,
$(C_1-C_6)$alkyl,
$(C_3-C_5)$cycloalkyl,
$(C_1-C_4)$alkylene-$(C_3-C_8)$cycloalkyl,
$(C_1-C_4)$alkylene-$(C_5-C_{10})$heteroaryl,
$(C_1-C_4)$alkylene-$(C_3-C_8)$heterocycloalkyl,
$C_1-C_4)$alkylene-$(C_6-C_{10})$aryl,
$(C_1-C_4)$alkylene-O—$(C_1-C_6)$alkyl, or
$C(O)NH$—$(C_1-C_6)$alkyl.
wherein $(C_1-C_6)$alkyl, $(C_3-C_8)$cycloalkyl, $(C_1-C_4)$alkylene, $(C_3-C_8)$heterocycloalkyl, $(C_6-C_{10})$aryl are unsubstituted or substituted.

In an even more preferred embodiment of a compound of formula (I)
$R_{11}$ is H or $(C_1-C_6)$alkyl; and
$R_{12}$ is
H,
$(C_1-C_6)$alkyl,
$(C_3-C_8)$cycloalkyl,
$(C_1-C_4)$alkylene-$(C_3-C_8)$cycloalkyl,
$(C_1-C_4)$alkylene-$(C_5-C_{10})$heteroaryl,
$(C_1-C_4)$alkylene-$(C_3-C_8)$heterocycloalkyl,
$(C_1-C_4)$alkylene-$(C_6-C_{10})$aryl, or
$(C_1-C_4)$alkylene-O—$(C_1-C_6)$alkyl.
wherein $(C_1-C_6)$alkyl, $(C_3-C_8)$cycloalkyl, $(C_1-C_4)$alkylene, $(C_3-C_8)$heterocycloalkyl, $(C_6-C_{10})$aryl are unsubstituted or substituted.

More preferrably $R_{11}$ is H, $(C_1-C_6)$alkyl and
$R_{12}$ is H, $(C_1-C_6)$alkyl or $(C_3-C_8)$cycloalkyl, wherein $(C_1-C_6)$alkyl or $(C_3-C_8)$cycloalkyl are unsubstituted or substituted, preferably unsubstituted.

In a further embodiment $R_{11}$ is H and
$R_{12}$ is H, $(C_1-C_6)$alkyl or $(C_3-C_8)$cycloalkyl
wherein $(C_1-C_6)$alkyl or $(C_3-C_8)$cycloalkyl are unsubstituted.

Most preferred $R_{11}$ and $R_{12}$ are H.

As examples for the before mentioned embodiments, $R_{11}$ or $R_{12}$ are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

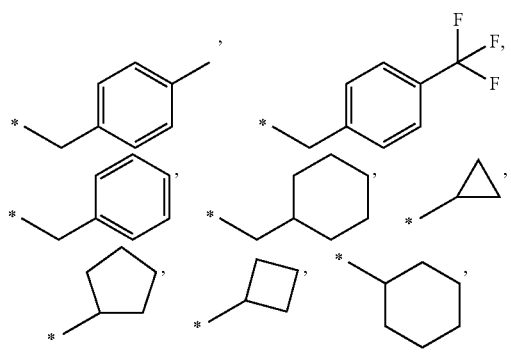

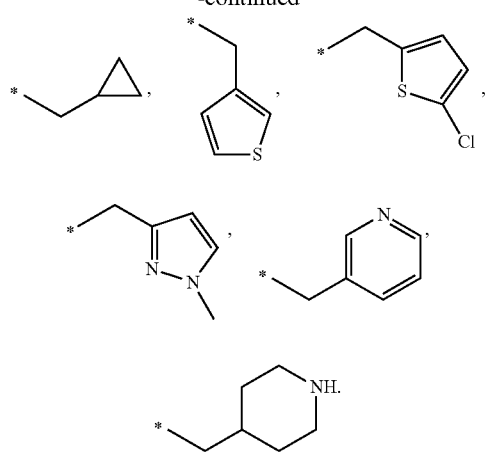

The asterisk (*) denotes where the bond is connected to the N-atom of the amine.

In one embodiment $R_{13}$ is H or $(C_1-C_6)$alkyl, which is unsubstituted or optionally substituted, more preferably $R_{13}$ is H or $(C_1-C_4)$alkyl, most preferably H. Preferably, the alkyl is unsubstituted.

In one embodiment of a compound of formula (I) the bicyclus formed with $R_6$ is selected from the group of

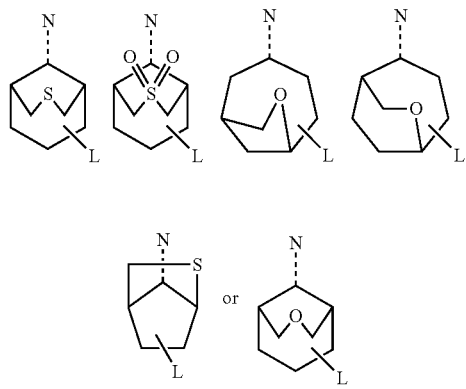

which is unsubstituted or optionally substituted by $R_9$.

(the dotted line with the N indicates the position of the $NR_{11}R_{12}$ residue)

In another embodiment of a compound of formula (I) the adamantane formed with $R_6$ is selected from the group of

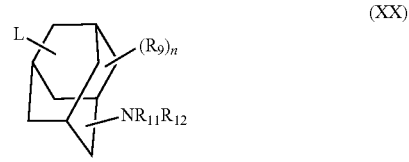

(XX)

which is unsubstituted or optionally substituted by residues $R_9$.

Preferably, the bicyclus or adamantane is unsubstituted (n is 0).

In one embodiment the adamantane formed has the following structure

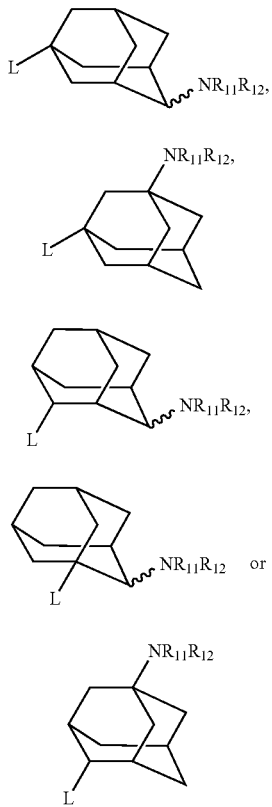

(XXa)

(XXb)

(XXc)

(XXd)

(XXe)

which is unsubstituted or optionally substituted by residues $R_9$.

A preferred embodiment of the adamantane formed with $R_6$ is a residue having the formula

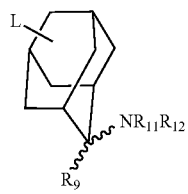

(XXI)

Particular embodiments for this residue are of the formula

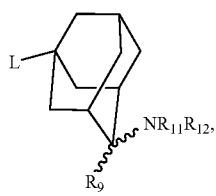

(XXIa)

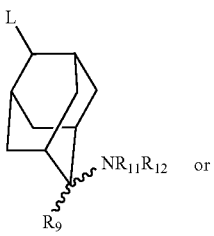

(XXIb)

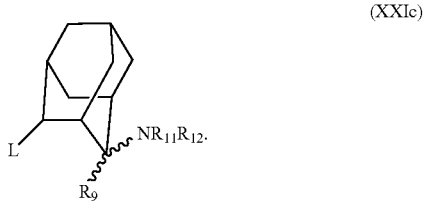

(XXIc)

The cis and trans isomers in the adamantane residues such as for example in the structures

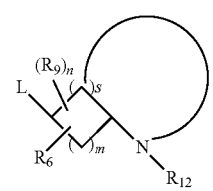

are included.

In another embodiment $R_6$ together with $R_{11}$ or $R_{12}$ and the N atom form a $(C_3-C_8)$heterocycloalkyl which is fused or connected as a spirocyclic ring system to the cycloalkyl residue to form a residue of the formula;

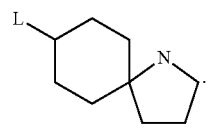

(XXI)

wherein said ring system is unsubstituted or optionally substituted by residues $R_9$;

Examples of residues formed by $R_6$ and $R_{11}$ are

In one embodiment m is 2 and s is 2. In another embodiment m is 3 and s is 1

In a further embodiment m is 2 and s is 1. In still another embodiment m is 3 and s is 0.

In yet another embodiment m is 4 and s is 0.

In one embodiment of a compound of formula (I) n is 0, 1, or 2. More preferred, n is 0 or 1. Most preferred n is 0.

In another embodiment L is O(CH$_2$)$_p$. In a further embodiment L is S(CH$_2$)$_p$, S(O)(CH$_2$)$_p$ or SO$_2$(CH$_2$)$_p$. In another embodiment L is NH(CH$_2$)$_p$, N[(C$_1$-C$_6$)alkyl](CH$_2$)$_p$, N[(C$_3$-C$_6$)cycloalkyl](CH$_2$)$_p$, N[(C$_1$-C$_3$)alkylene-aryl](CH$_2$)$_p$ or N[(C$_1$-C$_3$)alkylene-(C$_5$-C$_6$)heteroaryl](CH$_2$)$_p$ with NH(CH$_2$)$_p$, N(C$_1$-C$_6$)alkyl-(CH$_2$)$_p$ being more preferred. A preferred N(C$_1$-C$_6$)alkyl is N(C$_1$-C$_4$)alkyl, more preferably NCH$_3$ or NCH$_2$CH$_3$ with NCH$_3$ being more preferred. In a preferred embodiment L is O(CH$_2$)$_p$.

In another preferred embodiment L is S(CH$_2$)$_p$. In a further embodiment L is NH(CH$_2$)$_p$.

Most preferred L is O, S or NH with O being especially preferred.

Preferably p is 0, 1, 2, or 3, more preferred 0 or 1, with O being most preferred;

More preferably, L is O, S or NH, preferably L is O.

In a further embodiment the present invention relates to a compound of formula (I) selected from the group consisting of 6-(4-Amino-adamantan-1-yloxy)-7-chloro-2H-isoquinolin-1-one,
6-(4-Allyl-4-amino-adamantan-1-yloxy)-7-chloro-2H-isoquinolin-1-one,
6-(4-Amino-4-propyl-adamantan-1-yloxy)-7-chloro-2H-isoquinolin-1-one,
6-(4-Amino-4-methyl-adamantan-1-yloxy)-7-chloro-2H-isoquinolin-1-one,
6-(4-Amino-4-phenyl-adamantan-1-yloxy)-7-chloro-2H-isoquinolin-1-one,
6-(4-Amino-4-cyclopropyl-adamantan-1-yloxy)-7-chloro-2H-isoquinolin-1-one,
6-(4-Benzylamino-adamantan-1-yloxy)-7-chloro-2H-isoquinolin-1-one,
6-(3-Amino-adamantan-1-yloxy)-7-chloro-2H-isoquinolin-1-one,
6-(5-Amino-adamantan-2-yloxy)-7-chloro-2H-isoquinolin-1-one,
6-(5-Amino-adamantan-2-yloxy)-7-methyl-2H-isoquinolin-1-one,
6-{[(7-amino-3-oxabicyclo[3.3.1]non-9-yl]oxy}-7-chloroisoquinolin-1(2H)-one,
6-{[(7-amino-3-thiabicyclo[3.3.1]non-9-yl]oxy}-7-chloroisoquinolin-1(2H)-one
6-{[(7-amino-3-(dioxo-thia)bicyclo[3.3.1]non-9-yl]oxy}-7-chloroisoquinolin-1(2H)-one,
3,3-dioxide, or
6-(1-Aza-spiro[4.5]dec-8-yloxy)-7-chloro-2H-isoquinolin-1-one,
their stereoisomeric and/or tautomeric forms and/or their pharmaceutically acceptable salts thereof.

In a further embodiment a compound of formula (I) is selected from the group consisting of
cis-6-(5-Amino-adamantan-2-yloxy)-7-chloro-2H-isoquinolin-1-one,
trans-6-(5-Amino-adamantan-2-yloxy)-7-chloro-2H-isoquinolin-1-one,
6-{[(7-Endo,9-anti)-7-amino-3-oxabicyclo[3.3.1]non-9-yl]oxy}-7-chloroisoquinolin-1(2H)-one,
6-{[(7-endo,9-syn)-7-amino-3-oxabicyclo[3.3.1]non-9-yl]oxy}-7-chloroisoquinolin-1(2H)-one,
6-{[(7-Endo,9-anti)-7-amino-3-thiabicyclo[3.3.1]non-9-yl]oxy}-7-chloroisoquinolin-1(2H)-one,
6-{[(7-endo,9-syn)-7-amino-3-thiabicyclo[3.3.1]non-9-yl]oxy}-7-chloroisoquinolin-1(2H)-one, and
6-{[(7-Endo,9-anti)-7-amino-3-(dioxo-thia)bicyclo[3.3.1]non-9-yl]oxy}-7-chloroisoquinolin-1(2H)-one, 3,3-dioxide, their stereoisomeric and/or tautomeric forms and/or their pharmaceutically acceptable salts thereof.

In any embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

Isoquinoline substitution pattern is numbered according to IUPAC rules:

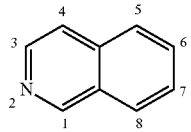

The terms isoquinolone and isoquinolinone are used synonymously.

All references to "compound(s) of formula (I)" herein refer to compound(s) of the formula (I), (II) (IIIa), (IIIb) and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The present invention also includes physiologically functional derivatives of a compound of formula (I). A physiologically functional derivative as used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I) in the form of their stereoisomeric forms, which include racemates, enantiomerically enriched mixtures, pure enantiomers and diastereomers and mixtures in any ratio thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention also relates to the compounds of the formula (I) and/or their pharmaceutically acceptable salts for use as pharmaceuticals (or medicaments), to the use of the compounds of the formula (I) and/or their pharmaceutically acceptable salts for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

In a further embodiment the invention also relates to the use of a compound of formula (I) and/or a pharmaceutically acceptable salt thereof for the treatment and/or prevention of hypertension, pulmonary hypertension, fibroid liver, liver failure, nephropathy, renal failure, chronic obstructive pulmonary disease (COPD), cerebral vasospasm, pain, spinal cord injury, erectile dysfunction, blood vessel restenosis, or cancer development and progression.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

Compounds of formula (I) may be made in the following manner:

Compounds of the general formula (I) can be assembled from a suitably substituted isoquinoline moiety and a suitably substituted cycloalkyl amine moiety.

Isoquinolines and isoquinolones like (i) or (ii), bearing a useful residue for coupling in 6-position, can be obtained by a wide variety of methods, for example reviewed in Alvarez et al. Science of Synthesis 2005, 15, 661-838 and 839-906 and references cited therein. Isoquinolines can also be converted to isoquinolones by methods described in the literature e.g. WO 2007/012421 or WO 2007/012422, like conversion of a suitable isoquinoline into the corresponding N-oxide with an oxidating agent like hydrogen peroxide or metachloro perbenzoic acid and subsequent conversion into the corresponding 1-chloro derivative by a chlorinating agent like phosphorous oxy chloride, followed by displacement of the chlorine by an alcohol under basic condition like sodium methoxide in methanol or conversion into the corresponding 2H-isoquinolone by for example treatment with ammonium acetate in acetic acid at elevated temperature. It is understood, that the hydroxyl-group in 6-position of (ii) can be liberated at a suitable stage of the synthesis e.g. from treatment of a corresponding 6-methoxy derivative with lewis acids like aluminium chloride or boron tribromide. It is furthermore understood, that 2H-isoquinolones can be converted into suitably protected 1-alkoxy isoquinolones by a variety of methods e.g. treatment of the corresponding 2H-isoquinolones with alkylating agents like benzyl bromide or methyl iodide in the presence of a suitable base like silver carbonate or triethyl amine in a suitable solvent like toluene or THF, or conversion of the said 2H-isoquinolones into their 1-chloro derivatives by treatment with a chlorinating agent like phosphorous oxychloride, followed by displacement of the chlorine by an alcohol e.g. under basic conditions like sodium methoxide in methanol. It is understood, that residues $R_3$, $R_4$, $R_5$, $R_7$, and/or $R_5$ can either be incorporated in the starting materials for the synthesis of the respective isoquinoline or isoquinolone or can be introduced at a suitable later stage e.g. by halogenation like bromination or chlorination and subsequent replacement of said halogen by methods well precedented in the literature like for example Suzuki or Hartwig Buchwald couplings using appropriate catalysts and coupling partners like boronic acids, amines or anilines.

One possible synthesis for a cycloalkyl amine substituted isoquinolinone (v) is described below in an exemplary fashion, but does not limit the present invention. The cycloalkyl amine substituted isoquinolinones (for example compound v) can by synthesized via a variety of methods. The following general scheme 1 illustrates some of the possible ways to access the isoquinolinones, but does not limit the present invention.

Scheme 1

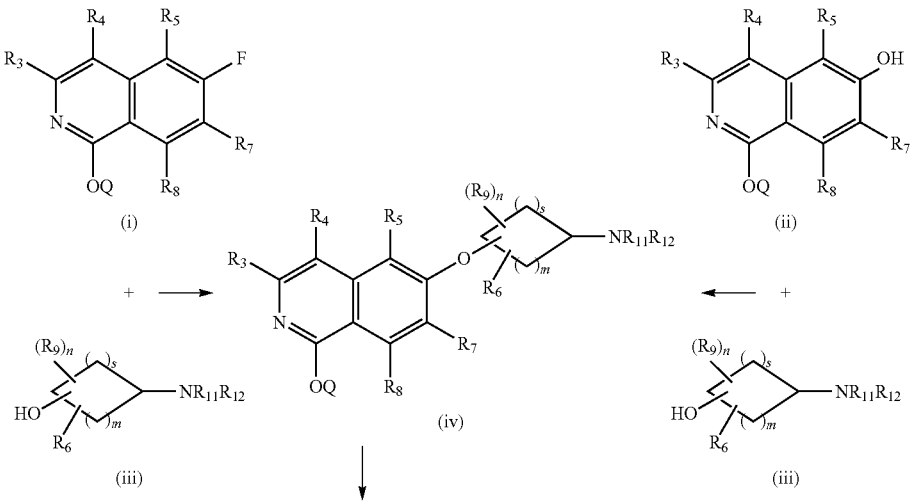

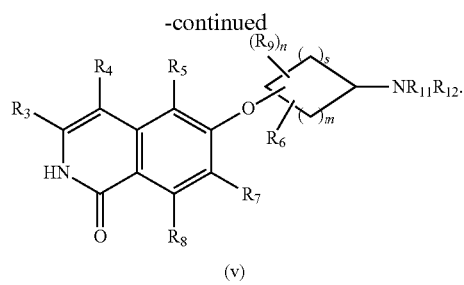

(v)

6-Fluoro-isoquinolones (i), for example substituted by $R_3$, $R_4$, $R_5$, $R_7$, and/or $R_8$ being for instance independently from each other substituents like hydrogen, alkyl, alkoxy or halide, can be reacted with suitable $R_{11}/R_{12}$ substituted amino alcohols wherein $R_{11}/R_{12}$ are independently from each other for example hydrogen, alkyl or a protecting group like for example Boc or Cbz in the presence of base such as DBU, cesium carbonate, or sodium hydride at temperatures ranging from ambient to 100° C. to give the corresponding derivatives (iv). Optionally, this conversion can already be performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

Alternatively, the amino alcohols can be coupled to 6-hydroxy-isoquinolones, such as (ii), under inversion of the hydroxyl bearing carbon center of compounds like (iii), either protected with a suitable protecting group Q or unprotected, via a Mitsunobu reaction using triphenylphosphine and dialkylazodicarboxylates such as diethylazodicarboxylate or diisopropylazodicarboxylate in a suitable solvent like tetrahydrofuran, or toluene. The products like (iv) obtained via these methods can then either be liberated to give compounds of type (v) or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step, like for example acidic removal of Boc-groups. Furthermore an amino group can be acylated by reacting it with a suitable acid chloride in the presence of a base like triethyl amine or Hünig's base or by reacting it with a suitable carboxylic acid in the presence of a base like triethylamine or Hünig's base and a coupling reagent like EDC, PyBOP or TOTU.

In case of use of protected isoquinolones, cleavage of the used protection groups is required to liberate the desired isoquinolone (v). This liberation, however, can be performed before or after the reductive amination step, depending on the nature of the used aldehyde/ketone and the protection group used.

Isoquinolone derivatives like (v) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The cycloalkyl amine moieties like for example (iii) can by synthesized via a variety of methods. The following general schemes illustrate some of the possible ways to access the amines, but do not limit the present invention. It is within the abilities of a person skilled in the art to replace the exemplary compounds shown in the schemes and exemplary reagent given in the text by appropriate alternative compounds or reagents or to omit or add synthetic steps when appropriate.

The synthesis of a cycloalkyl aminoalcohol (iii) is described exemplary in scheme 2 but does not limit the scope of substituents in the present invention.

A cycloalkyl amine moiety (iii) can for example be accessed from a suitable diketone, which is mono-ketalized to give a compound (vi) by treatment with a suitable diol like ethylene glycol in the presence of an acid like p-toluene sulfonic acid. It is understood, that (vi) can for example also be obtained by mono-deprotection of a corresponding diketal or oxidation of a suitable alcohol precursor to a corresponding ketone by reaction with a suitable oxidizing agent like for example mangane or chromium reagents or hypervaltent iodine reagents. (iv) can then for example be converted into amines of type (vii) by reaction with an amine like ammonia, benzyl amine or ethyl amine in the presence of a reducing agent like sodium cyano borohydride or sodium borohydride, possibly in the presence of a lewis acid. Ketone (viii) can be obtained for example by treatment of (vii) under acidic conditions like actone and hydrochloric acid or aqueous acetic acid at elevated temperature. The ketone can then be converted in an alcohol (iii) by reaction with a suitable reductive agents like sodium borohydride in a suitable solvent like methanol, ethanol or THF.

Scheme 2

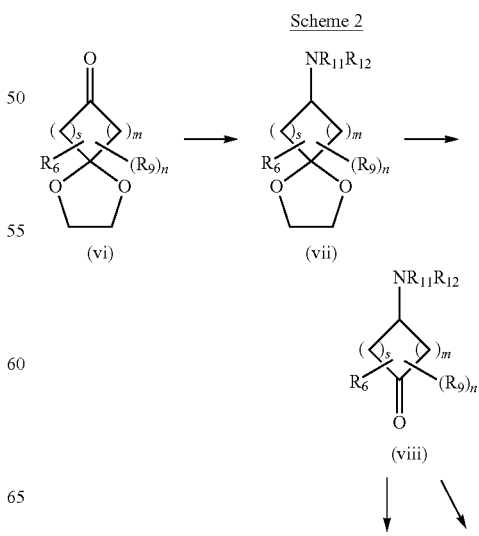

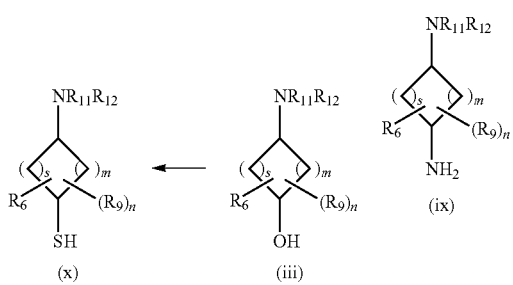

For instance, the hydroxy functionality of a compound (iii) can be converted to a thiol via a Mitsunobu reaction using thioacetate and subsequent basic cleavage with a suitable base, leading to amino moieties of type (x). These thiols can—after coupling to suitable isoquinolinones under useful reaction conditions like for example in a similar fashion as described above in scheme 1 for the coupling of (iii)—then be used to obtain compounds of formula (I) with the linker unit L=S—or optionally be oxidized via methods known to the person skilled in the art to the corresponding sulfoxides and sulfones (for obtaining compounds of formula (I) with the linker unit L=SO and SO$_2$). The corresponding amines can be accessed via a reductive amination step starting from ketones such as compound (viii) using suitable amines in the presence of a reducing agent like sodium triacetoxy borohydride, sodium borohydride or sodium cyanoborohydride in the presence of a water withdrawing agent like molecular sieves or a suitable ortho ester.

One option to introduce residues R$_9$ in α-position of the amine is to react a suitably protected ketone like (vi) with an amine source like ammonia and a suitable organometallic reagent like allyl boranes in a suitable solvent. Another option is to react protected alcohols (xii) with a reagent like 2-methyl-2-propanesulfinamide to a corresponding sulfimine (xiii) which can be further reacted with a suitable organometallic reagent like aryl lithium or Grignard reagents to give amines of type (xiv), which then can be further derivatized.

Another option is to construct bicyclic or polycyclic carbocyclic acid derivatives containing keto moieties or protected keto moieties like (xv) by a Curtius reaction, e.g. by first converting the acid into an acyl azide by treatment with a chlorinating agent like sulfuryl chloride or thionyl chloride and subsequent reaction with an azide source like sodium azide in a suitable solvent and subsequent reaction of said acid chloride at elevated temperature to give the corresponding isocyanate, which can be trapped with a suitable alcohol like benzyl alcohol to give the corresponding carbamate protected amine. Compound (xvi) can then be further converted.

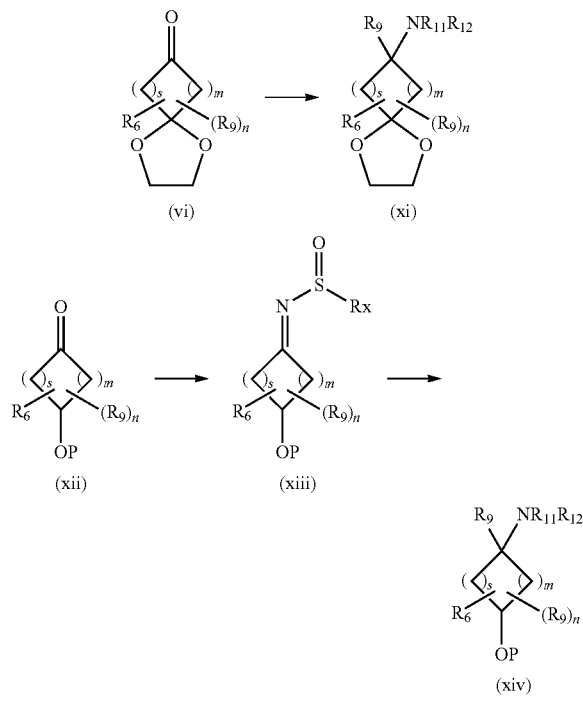

Scheme 3.

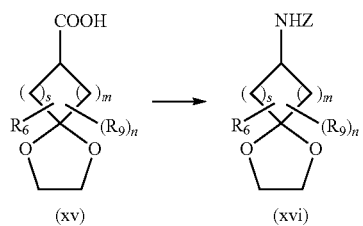

Scheme 4.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formula (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as NMR, IR and mass spectrometry (MS) can be used for characterizing a compound of the invention.

EXAMPLES

The following examples illustrate the various embodiments of the present invention and are part of the present invention.

1-Benzyloxy-7-chloro-6-fluoro-isoquinoline (1)

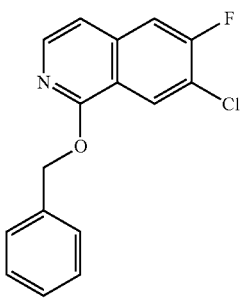 [SMILES: Fc1cc2ccnc(OCc3ccccc3)c2cc1Cl]

7-Chloro-6-fluoro-2H-isoquinolin-1-one (prepared according to WO 2007/012422; 52.2 g) was dissolved in THF (1 L). After addition of silver carbonate (145.5 g) and benzyl bromide (40.6 mL), the mixture was stirred at room temperature overnight. Another 6.2 mL of benzyl bromide were added and the mixture was stirred at 70° C. for 2 h. After cooling down to room temperature, the reaction mixture was diluted by addition of 1 L of ethyl acetate and filtered over celite. The filter cake was washed thoroughly, the organic layer was evaporated and subjected to silica gel chromatography (n-heptanes: methyl tert. butyl ether) to give 27.8 g of the title compound 1. $R_t$=3.73 min (Method 1). Detected mass: 288.1 (M+H$^+$).

1-Benzyloxy-6-fluoro-7-methyl isoquinoline (2)

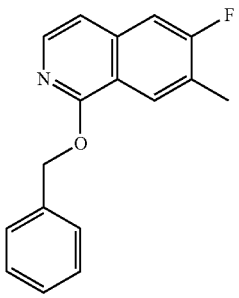 [SMILES: Cc1cc2c(OCc3ccccc3)nccc2cc1F]

6-Fluoro-7-methyl-2H-isoquinolin-1-one (prepared as described in WO2007012421, 13.2 g, mmol) was dissolved in tetrahydrofurane (175 mL). After addition of silver carbonate (41.2 g), benzyl bromide (15.3 g) was added dropwise. The mixture was stirred overnight. The mixture was heated to 70° C. and another 3 mL of benzyl bromide were added. Heating was continued until no further conversion was observed. The mixture was taken up in ethyl acetate, filtered over celite, evaporated and the residue was taken up in little ethyl acetate. The formed precipitate was filtered off to give 3.0 g of (2). The mother liquor was concentrated and chromatographed on silica gel to yield another 8.6 g of (2). $R_t$=4.00 min (Method 2). Detected mass: 268.1 (M+H$^+$).

4-Allyl-4-amino-adamantan-1-ol (3)

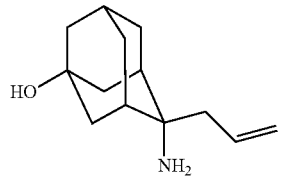

5-Hydroxy-2-adamantanone (3.0 g, 18.1 mmol) was dissolved in a solution of ammonia in methanol (7N, 26 mL, 180 mmol, 10 eq.) and stirred for 15 min at room temperature. Then, 2-allyl-4,4,5,5-tetramethyl-1,3,2-dioxa-borolane (5.4 mL, 28.9 mmol, 1.6 eq.) was added dropwise. The reaction mixture was stirred for 16 h at room temperature before the volatiles were removed in vacuo. The residue was taken up in methanol twice and evaporated, then lyophilized from water to give 4-allyl-4-amino-adamantan-1-ol (3) as a mixture of diastereomers. $R_t$=1.05 min, 1.79 min (Method 2). Detected mass: 270.3 (M+H$^+$).

4-Propyl-4-amino-adamantan-1-ol (4)

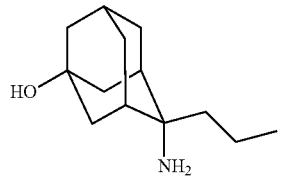

A solution of 4-allyl-4-amino-adamantan-1-ol (3, 3.6 g, 17.4 mmol) in methanol (50 mL) was treated with 50 mg of 10% palladium on activated carbon and the mixture was stirred overnight under a hydrogen atmosphere (1 atm) at room temperature. The catalyst was removed by filtration, and the filtrate was evaporated in vacuo to give 2.8 g of the title compound as diastereomeric mixture (4). $R_t$=0.21 min, 0.73 min (Method 3). Detected mass: 210.2 (M+H$^+$).

2-Methyl-propane-2-sulfinic acid [5-(tert-butyl-dimethyl-silanyloxy)-adamantan-(2E)-ylidene]-amide (5)

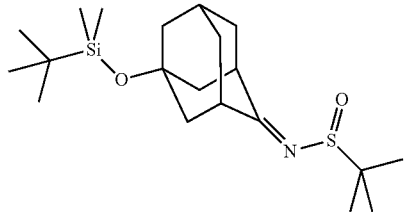 [SMILES: CC(C)(C)S(=O)N=C1C2CC3CC1CC(O[Si](C)(C)C(C)(C)C)(C3)C2]

To a solution of 5-(tert-butyl-dimethyl-silanyloxy)-adamantan-2-one (1.00 g, 3.57 mmol) in tetrahydrofuran (2.5 mL) was added titanium(IV) ethoxide (1.12 mL, 5.35 mmol, 1.5 eq.) and 2-methyl-2-propanesulfinamide (454 mg, 3.74 mmol, 1.05 eq.). The resulting mixture was stirred for 6 h under reflux and 16 h at room temperature, before being poured into an equal volume of saturated aqueous NaHCO$_3$ solution with rapid stirring and filtered through celite. The filter cake was washed with ethyl acetate, the aqueous layer was separated and extracted twice with ethyl acetate. The combined organic layers were dried over MgSO$_4$, filtered, and concentrated under vacuum to give 1.00 g of the title compound (5). R$_t$=2.25 min (Method 3). Detected mass: 384.3 (M+H$^+$).

2-Methyl-propane-2-sulfinic acid [5-(tert-butyl-dimethyl-silanyloxy)-2-phenyl-adamantan-2-yl]-amide (6)

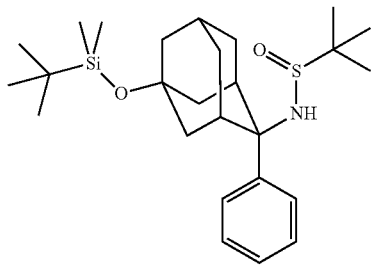 [SMILES: CC(C)(C)S(=O)NC1(c2ccccc2)C2CC3CC1CC(O[Si](C)(C)C(C)(C)C)(C3)C2]

A solution of 2-methyl-propane-2-sulfinic acid [5-(tert-butyl-dimethyl-silanyloxy)-adamantan-(2E)-ylidene]-amide (5, 1.50 g, 3.91 mmol) in diethyl ether (10 mL) was added dropwise to a 0.5 M solution of phenylmagnesium chloride in diethyl ether (17.2 mL, 8.60 mmol, 2.2 eq.) precooled to −78° C. The reaction solution was allowed to warm to room temperature overnight. Another equivalent of phenylmagnesium chloride was added (1.8M in diethylether, 2.2 mL) and the reaction mixture stirred for further 2 h. The reaction was cooled to 0° C., quenched by dropwise addition of saturated aqueous Na$_2$SO$_4$ solution, dried over MgSO$_4$, filtered, and concentrated under vacuum. The crude product was purified by silica gel chromatography to yield 1.41 g of the title compound (6) as diastereomeric mixture. R$_t$=5.19 min (Method 4). Detected mass: 462.2 (M+H$^+$).

4-Phenyl-4-amino-adamantan-1-ol (7)

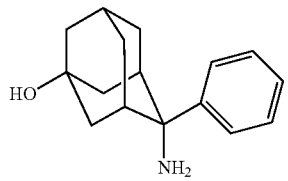 [SMILES: NC1(c2ccccc2)C2CC3CC1CC(O)(C3)C2]

To a solution of 2-methyl-propane-2-sulfinic acid [5-(tert-butyl-dimethyl-silanyloxy)-2-phenyl-adamantan-2-yl]-amide (6) in 2-propanol (10 mL) was added 1N hydrochloric acid (5 mL) and the mixture was stirred at room temperature until complete conversion was achieved. The reaction mixture was washed with diethyl ether, the aqueous phase was concentrated in vacuo and lyophilized to yield 676 mg of a diastereomeric mixture of 4-phenyl-4-amino-adamantan-1-ol (7) as its hydrochloride. R$_t$=0.33 min, 0.85 min (Method 3). Detected mass: 227.2 (M-NH$_3$+H$^+$).

The following products were synthesized as mixture of diastereomers as their hydrochlorides as described for the synthesis of 7 starting from 2-methyl-propane-2-sulfinic acid [5-(tert-butyl-dimethyl-silanyloxy)-adamantan-(2E)-ylidene]-amide (5) and the respective Grignard reagents.

| Comp. No. | Product | Chemical Name | [M + H$^+$] | R$_t$/ [min] | Method |
|---|---|---|---|---|---|
| 8 | | 4-Methyl-4-amino-adamantan-1-ol | 182 | 0.18, 0.52 | 3 |
| 9 | | 4-Cyclopropyl-4-amino-adamantan-1-ol | 191 [M − NH$_3$ + H$^+$] | 0.19, 0.66 | 3 |

Synthesis of 5-Amino-adamantan-2-ol (14)

a) 4-Oxo-adamantane-1-carboxylic acid methyl ester (10)

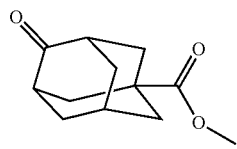

38 mL of fuming sulfuric acid were placed in a two necked flask and warmed to 60° C. 1.5 g of 5-hydroxy-2-adamantanone, dissolved in formic acid (8.5 ml) were added dropwise over the course of 2 h. Another 9 mL of formic acid were added over a period of 2 h and stirring was continued at 60° C. for 1 h and at room temperature overnight. Under ice cooling, the reaction mixture was poured on 100 mL of dry methanol, stirred at room temperature for 2 h and subsequently poured onto 400 mL of ice. The aqueous layer was extracted with dichloromethane three times, the combined organic layer was dried over sodium sulphate and evaporated to dryness to give 1.64 g of the desired product. $R_t$=1.75 min (5). Detected mass: 209.2 (M+H$^+$).

b) 4-Oxo-adamantane-1-carboxylic acid (11)

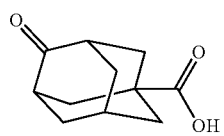 [SMILES: O=C1C2CC3CC1CC(C(=O)O)(C3)C2]

1.64 g of 4-Oxo-adamantane-1-carboxylic acid methyl ester (10) were dissolved in 4 mL of 2M aq. LiOH/MeOH (1:1) and stirred overnight at room temperature. Additional 5 ml of the MeOH/LiOH mixture were added and stirring was continued until conversion was complete. The reaction mixture was acidified and extracted three times with ethyl acetate. The organic layer was dried over sodium sulphate and evaporated to dryness to give 1.4 g of (11) as a solid. $R_t$=0.87 min (Method 3). Detected mass: 195.2 (M+H$^+$).

c) (4-Oxo-adamantan-1-yl)-carbamic acid benzyl ester (12)

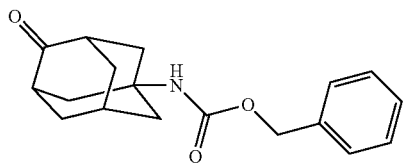 [SMILES: O=C(NC12CC3CC(C1)C(=O)C(C3)C2)OCc1ccccc1]

0.7 g of 4-Oxo-adamantane-1-carboxylic acid (11) were codistilled twice with toluene and dissolved in 5.5 mL of dry toluene. 1.1 mL of triethylamine were added. At 0° C., 0.9 mL of diphenylphosphoryl azide were added dropwise. The mixture was allowed to warm to room temperature and then the mixture was put into a preheated bath at 90° C. The mixture was heated until gas evolution ceased (ca. 1.5 h). 1.9 mL of benzyl alcohol were added and stirring was continued at 100° C. When the reaction was complete, it was cooled to room temperature, then ethyl acetate was added and the mixture was extracted twice with 1M aqueous sodium carbonate solution. The aqueous layer was extracted with ethyl acetate and the combined organic layer was dried over sodium sulphate and evaporated. The resulting oil was subjected to silica gel chromatography (heptanes:ethyl acetate) to give 871 mg of the desired product. $R_t$=1.40 min (Method 3). Detected mass: 300.2 (M+H$^+$).

d) (4-Hydroxy-adamantan-1-yl)-carbamic acid benzyl ester (13)

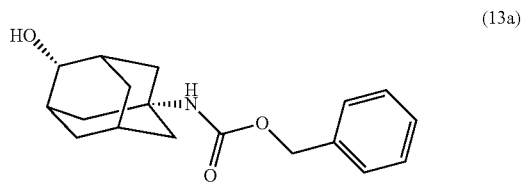

(13a)

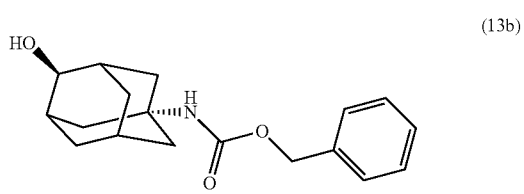

(13b)

865 mg of (4-Oxo-adamantan-1-yl)-carbamic acid benzyl ester (12) were dissolved in 15 mL of THF and 109 mg of sodium borohydride were added at 0° C. Stirring was continued for 2 h, then the reaction mixture was acidified by addition of 2M HCl. The reaction mixture was extracted three times with ethyl acetate and the combined organic layer was dried over sodium sulphate and evaporated. The resulting oil was subjected to HPLC separation to give 463 mg of the desired product as a cis/trans mixture along with 119 mg of the cis derivative (13a) and 10 mg of the trans derivative (13b). 13a: $R_t$=1.37 min (Method 3). Detected mass: 302.3 (M+H+). 13b: $R_t$=1.39 min (Method 3). Detected mass: 302.3 (M+H$^+$);

e) 5-Amino-adamantan-2-ol (14)

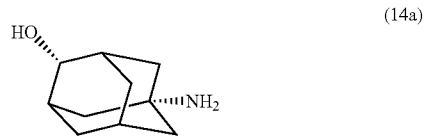

(14a)

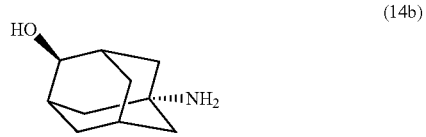

(14b)

113 mg of (13a) were dissolved in 13.5 mL of methanol and 15 mg of 10% Pd on charcoal were added. Stirring under an atmosphere of hydrogen was continued for 3 h until the reaction was complete. The catalyst was filtered off and the resulting organic layer was evaporated to give 63 mg of the desired product. $R_t$=0.36 min (Method 3). Detected mass: 168.2 (M+H$^+$).

In an analogous fashion, (13b) and the cis/trans mixture (13) could be deprotected to give the respective aminoalcohols (14b and 14) used for coupling.

Synthesis of 6-(4-Amino-adamantan-1-yloxy)-7-chloro-2H-isoquinolin-1-one (Example 1 and Example 2)

a) 5-(1-Benzyloxy-7-chloro-isoquinolin-6-yloxy)-adamantan-2-ylamine (15)

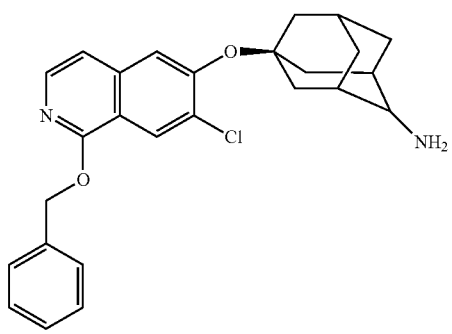

To a suspension of sodium hydride (60% in mineral oil, 417 mg, 10.4 mmol, 3 eq.) in dimethyl acetamide (7 mL) was added a solution of 4-amino-adamantan-1-ol (640 mg, 3.82 mmol, 1.1 eq.) in dimethyl acetamide (7 mL). After stirring for 60 min at room temperature, a solution of 1-benzyloxy-7-chloro-6-fluoro-isoquinoline (1, 1.0 g, 3.48 mmol) in dimethyl acetamide (7 mL) was added and stirring was continued at room temperature until the reaction went to completion. The reaction was quenched by addition of water (15 mL) and the reaction mixture was extracted twice with a mixture of dichloromethane and 2-propanol (3:1). The combined organic layers were evaporated, water was added and the mixture was subjected to lyophilization to remove remainders of dimethyl acetamide. The obtained crude product was purified by flash chromatography (SiO$_2$, 0%→30% methanol in dichloromethane) to yield 473 mg of the title compound as diastereomeric mixture. R$_t$=1.35 min, 1.55 min (Method 3). Detected mass: 435.2 (M+H$^+$).

b) 6-(4-Amino-adamantan-1-yloxy)-7-chloro-2H-isoquinolin-1-one (Example 1 and Example 2)

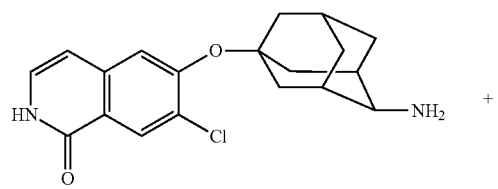

+

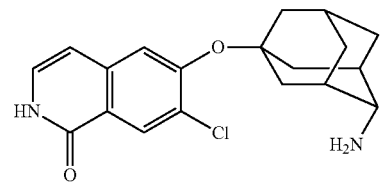

A solution of 5-(1-benzyloxy-7-chloro-isoquinolin-6-yloxy)-adamantan-2-ylamine (15, 473 mg) in 2-propanol (4 mL) was treated with 1N aqueous hydrochloric acid (2 mL) and stirred at room temperature until complete conversion was observed. The reaction mixture was evaporated and lyophilized from water twice to yield 385 mg of crude product. Purification by preparative HPLC and lyophilization from 1N HCl and water gave 10 mg of the pure diastereoisomer Example 1 and 11 mg of Example 2 as their respective hydrochlorides along with further material as mixture of isomers. Example 1: R$_t$=2.40 min (Method 4). Detected mass: 345.1 (M+H$^+$); Example 2: 2.38 min (Method 2). Detected mass: 345.1 (M+H$^+$). The relative stereochemistry was not assigned.

The following examples were synthesized as hydrochlorides from the respective aminoadamantanols, that were either commercial (for Example 13), their synthesis described above (for Example 3-11 and 14 and 15) or synthesized as described above, and 1-benzyloxy-7-chloro-6-fluoro-isoquinoline (1) using a similar procedure as described for example Example 1. In case of Example 16, 1-benzyloxy-7-methyl-6-fluoro-isoquinoline (2) was used as isoquinoline building block.

If the diastereoisomers could not be separated on an earlier stage of the synthesis, the deprotected products were purified by preparative HPLC and lyophilized from 1N HCl and water, respectively. In the case of Example 14 and Example 15 (synthesized from the cis/trans mixture (13), it was possible to separate the cis/trans isomers after coupling in step a) by silica gel chromatography (dichloromethane/methanol) as the O-benzyl protected isoquinolinones.

For Example 3 to 10 the relative stereochemistry was not assigned.

| Ex.-No. | Product | Isomer | Chemical Name | [M + H$^+$] | R$_t$/[min] | Method |
|---|---|---|---|---|---|---|
| 3 | | 1 | 6-(4-Allyl-4-amino-adamantan-1-yloxy)-7-chloro-2H-isoquinolin-1-one | 385.2 | 1.10 | 1 |

-continued

| Ex.-No. | Product | Isomer | Chemical Name | [M + H⁺] | $R_t$/[min] | Method |
|---|---|---|---|---|---|---|
| 4 | | 2 | 6-(4-Allyl-4-amino-adamantan-1-yloxy)-7-chloro-2H-isoquinolin-1-one | 385.2, 368.1 [M − NH₃ + H⁺] | 2.05 | 2 |
| 5 | | 1 | 6-(4-Amino-4-propyl-adamantan-1-yloxy)-7-chloro-2H-isoquinolin-1-one | 370.1 [M − NH₃ + H⁺] | 2.59 | 4 |
| 6 | | 2 | 6-(4-Amino-4-propyl-adamantan-1-yloxy)-7-chloro-2H-isoquinolin-1-one | 370.2 [M − NH₃ + H⁺] | 2.41 | 2 |
| 7 | | 1 | 6-(4-Amino-4-methyl-adamantan-1-yloxy)-7-chloro-2H-isoquinolin-1-one | 359.2, 342.1 [M − NH₃ + H⁺] | 2.17 | 2 |
| 8 | | 2 | 6-(4-Amino-4-methyl-adamantan-1-yloxy)-7-chloro-2H-isoquinolin-1-one | 342.1 [M − NH₃ + H⁺] | 2.23 | 2 |
| 9 | | 1 | 6-(4-Amino-4-phenyl-adamantan-1-yloxy)-7-chloro-2H-isoquinolin-1-one | 404.2 [M − NH₃ + H⁺] | 2.41 | 2 |
| 10 | | 2 | 6-(4-Amino-4-phenyl-adamantan-1-yloxy)-7-chloro-2H-isoquinolin-1-one | 421.2, 404.2 [M − NH₃ + H⁺] | 2.59 | 2 |

-continued

| Ex.-No. | Product | Isomer | Chemical Name | [M + H+] | Rf/[min] | Method |
|---|---|---|---|---|---|---|
| 11 | | 1 + 2 | 6-(4-Amino-4-cyclopropyl-adamantan-1-yloxy)-7-chloro-2H-isoquinolin-1-one | 368.2 [M − NH3 + H+] | 0.94, 0.99 | 3 |
| 12 | | 1 + 2 | 6-(4-Benzylamino-adamantan-1-yloxy)-7-chloro-2H-isoquinolin-1-one | 435.2 | 2.45, 2.53 | 2 |
| 13 | | | 6-(3-Amino-adamantan-1-yloxy)-7-chloro-2H-isoquinolin-1-one | 345.1 | 0.93 | 3 |
| 14 | | 1 | Cis-6-(5-Amino-adamantan-2-yloxy)-7-chloro-2H-isoquinolin-1-one | 345.2 | 1.87 | 2 |
| 15 | | 2 | Trans-6-(5-Amino-adamantan-2-yloxy)-7-chloro-2H-isoquinolin-1-one | 345.2 | 1.92 | 2 |

| Ex.-No. | Product | Isomer | Chemical Name | [M + H⁺] | R$_t$/ [min] | Method |
|---|---|---|---|---|---|---|
| 16 | 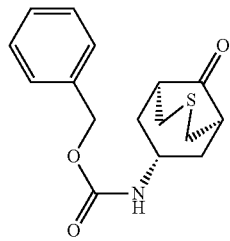 [SMILES: O=C(N[C@H]1C[C@H]2CSC[C@@H](C1)C2=O)OCc1ccccc1] | 1 + 2 | 6-(5-Amino-adamantan-2-yloxy)-7-methyl-2H-isoquinolin-1-one | 325.2 | 1.87 | 2 |

(9-Oxo-3-thia-bicyclo[3.3.1]non-7-yl)-carbamic acid benzyl ester (16)

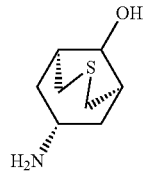

a) A mixture of triethylamine (10.1 ml, 72 mmol) and 3,6-dihydro-4-(1-pyrrolidinyl)-2H-thiopyran (12.9 g, 76 mmol, prepared according to a procedure described in Tetrahedron Asymmetry 1997, 1811-1820) in anhydrous acetonitrile (55 ml) was heated to reflux, then ethyl 3-bromo-2-(bromomethyl)propionate (14.6 g, 53 mmol) in dry acetonitrile (42 ml) was added dropwise over a period of 45 min. The resulting reaction mixture was refluxed for another 1.5 hours, then cooled to room temperature before a 10% aqueous acetic acid solution (5.2 ml) was added. The mixture was then refluxed for 1 hour and evaporated to dryness. Brine was added to the residue, the aqueous phase was extracted with ethyl acetate, the combined organic extracts were dried over anhydrous sodium sulphate, filtered and concentrated in vacuo to yield 9-oxo-3-thia-bicyclo[3.3.1]nonane-7-carboxylic acid ethyl ester as a brown oil (15.5 g).

b) To a solution of 9-oxo-3-thia-bicyclo[3.3.1]nonane-7-carboxylic acid ethyl ester (5 g, 22 mmol) in a THF (55 ml)/water (30 ml) mixture at 0° C. was added dropwise a 1N sodium hydroxide solution (24 ml, 24 mmol). The reaction mixture was stirred at room temperature overnight, then heated to 60° C. for 1 hour before THF was evaporated. The remaining aqueous layer was washed with ethyl acetate, acidified with 1N HCl, the resulting precipitate was filtered and dried to yield 9-oxo-3-thia-bicyclo[3.3.1]nonane-7-carboxylic acid (2.22 g) as a solid.

c) A mixture of 9-oxo-3-thia-bicyclo[3.3.1]nonane-7-carboxylic acid (2.22 g, 11 mmol), triethylamine (1.7 ml, 12 mmol) and diphenyl phosphoryl azide (2.6 ml, 12 mmol) in dry toluene (20 ml) was stirred at room temperature for 2 hours, then refluxed for another 2 hours and cooled to room temperature. Benzylic alcohol (11.4 ml, 110 mmol) was added, the solution was refluxed overnight, and evaporated to dryness. Water was added to the residue and the aqueous layer was extracted with ethyl acetate. The combined organic layers were dried over anhydrous sodium sulphate, filtered and concentrated under reduced pressure to give the crude product. The residue was purified by silica gel chromatography (cyclohexane:ethyl acetate 1:1) to yield crude (9-oxo-3-thia-bicyclo[3.3.1]non-7-yl)-carbamic acid benzyl ester (16, 4.5 g). R$_t$=4.6 min (Method 6), Detected mass: 306.1 (M+H⁺), (7-endo)-7-amino-3-oxabicyclo[3.3.1]nonan-9-ol (17)

a) To a solution of (9-oxo-3-thia-bicyclo[3.3.1]non-7-yl)-carbamic acid benzyl ester (16, 4.2 g, 13.7 mmol) in ethanol (172 ml) was added sodium borohydride (0.78 g, 20.6 mmol) portionwise at room temperature. The solution was stirred for 1 hour before addition of sodium borohydride (0.2 g, 5 mmol). The reaction mixture was stirred for 2 days, a further portion of sodium borohydride (0.340 g, 9 mmol) was added, and stirring was continued for 4 hours. The mixture was then concentrated under reduced pressure and cold water was added to the residue as well as dichloromethane. After a extraction of the aqueous phase with dichlormethane, the combined organic layer was dried over anhydrous sodium sulphate, filtered and concentrated under reduced pressure. The crude product was purified by silica gel chromatography (cyclohexane:ethyl acetate 40:60) to yield 9-hydroxy-3-thia-bicyclo[3.3.1]non-7-yl)-carbamic acid benzyl ester as a white solid (0.84 g).

b) A solution of (9-hydroxy-3-thia-bicyclo[3.3.1]non-7-yl)-carbamic acid benzyl ester (0.19 g, 0.63 mmol) in 6N HCl (0.3 ml, 1.8 mmol) was refluxed for 1 hour. The reaction mixture was then cooled to room temperature and co-evaporated with toluene to give the title compound as its hydrochloride as a colourless oil (110 mg). Detected mass: 173 (m/z, EI).

(7-endo)-7-amino-3-oxabicyclo[3.3.1]nonan-9-ol, 3,3-dioxide (18)

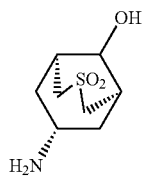

To a solution of 9-hydroxy-3-thia-bicyclo[3.3.1]non-7-yl)-carbamic acid benzyl ester (17, step a, 1.5 g, 4.47 mmol) in anhydrous chloroform (28 ml) was added 3-chloroperbenzoic acid (1.54 g, 8.9 mmol). The resulting mixture was stirred at room temperature overnight, then refluxed for 3 hours before another portion of 3-chloroperbenzoic acid (0.75 g, 4.3 mmol) was added. The reaction mixture was refluxed for another 3 hours, then poured onto water and extracted with chloroform. The organic layer was washed with a sodium sulfite solution and water before being dried over anhydrous sodium sulphate, filtered and concentrated under reduced pressure to afford the crude product which was used in the next step without any further purification. To 1.15 g of the obtained material in anhydrous methanol (170 ml) was added palladium hydroxide (20% on activated carbon, 0.093 g). The reaction mixture was vigorously stirred under hydrogen atmosphere (1 bar) for 4 hours before it was filtered. Palladium hydroxide (0.47 g) was added to the filtrate, the resulting suspension was stirred under hydrogen atmosphere (3 bars) for one hour before being filtered. The filtrate was concentrated in vacuo to yield 0.58 g of the title compound (18) as a gum which was used in the next step without any further purification. $R_t$=0.40 min (Method 7). Detected mass: 206 (M+H$^+$).

(7-Endo)-7-amino-3-oxabicyclo[3.3.1]nonan-9-ol (19)

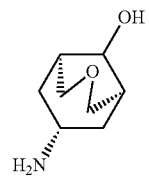

Starting from 1-(3,6-dihydro-2H-pyran-4-yl)pyrrolidine (obtained following a published procedure in Tetrahedron Asymmetry 1997, 1811-1820), the title compound was prepared in a similar fashion as the reaction sequence described for the synthesis of (7-endo)-7-amino-3-oxabicyclo[3.3.1]nonan-9-ol (17). Detected mass: 157 (m/z, EI).

The following examples were synthesized as hydrochlorides from the respective aminoadamantanols and 1-benzyloxy-7-chloro-6-fluoro-isoquinoline (1) using a similar procedure as described for Example 01. The cis/trans isomers were separated after coupling in step a) by silica gel chromatography (dichloromethane/methanol) as the O-benzyl protected isoquinolinones.

| Ex.-No. | Product | Chemical Name | [M + H$^+$] | $R_t$/[min] | Method |
|---|---|---|---|---|---|
| 17 | | 6-{[(7-Endo,9-anti)-7-amino-3-oxabicyclo[3.3.1]non-9-yl]oxy}-7-chloroisoquinolin-1(2H)-one | 335 | 3.90 | 8 |
| 18 | | 6-{[(7-endo,9-syn)-7-amino-3-oxabicyclo[3.3.1]non-9-yl]oxy}-7-chloroisoquinolin-1(2H)-one | 335 | 4.04 | 8 |
| 19 | | 6-{[(7-Endo,9-anti)-7-amino-3-thiabicyclo[3.3.1]non-9-yl]oxy}-7-chloroisoquinolin-1(2H)-one | 351 | 2.82 | 8 |
| 20 | | 6-{[(7-endo,9-syn)-7-amino-3-thiabicyclo[3.3.1]non-9-yl]oxy}-7-chloroisoquinolin-1(2H)-one | 351 | 2.94 | 8 |

| Ex.-No. | Product | Chemical Name | [M + H⁺] | R$_t$/[min] | Method |
|---|---|---|---|---|---|
| 21 | 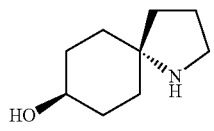 | 6-{[(7-Endo,9-anti)-7-amino-3-(dioxo-thia)bicyclo[3.3.1]non-9-yl]oxy}-7-chloroisoquinolin-1(2H)-one, 3,3-dioxide | 383.1 | 0.50 | 9 |

Trans-1-aza-spiro[4.5]decan-8-ol (20)

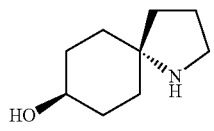

A solution of 669 mg (1.62 mmol) of 9-benzyl-11-iodo-1,4-dioxa-9-aza-dispiro[4.2.4.2]tetradecane (prepared starting from 1,4-dioxa-spiro[4.5]decan-8-one according to the procedure published in J. Bonjoch et al., Tetrahedron Lett. 2003, 44, 8387) in methanol (30 mL) was treated with 50 mg of 20% palladium hydroxide on activated carbon and the mixture was stirred overnight under a hydrogen atmosphere (1 atm) at room temperature. The catalyst was removed by filtration, and the filtrate was evaporated in vacuo to give crude 9-benzyl-1,4-dioxa-9-aza-dispiro[4.2.4.2]tetradecane, which was directly dissolved in a 1:1 mixture of acetone and 6N aqueous hydrochloric acid (10 mL) and stirred at room temperature. After the reaction went to completion, the mixture was poured onto a saturated aqueous sodium bicarbonate solution and extracted twice with ethyl acetate. The combined organics were washed with brine and water, dried over sodium sulphate, filtered and concentrated. Purification by flash chromatography (SiO$_2$, 0%→100% ethylacetate in heptane) gave 180 mg (0.74 mmol) of 1-benzyl-1-aza-spiro[4.5]decan-8-one, which was dissolved in ethanol (10 mL) and cooled to 0° C. Then, sodium borohydride (14 mg, 0.37 mmol, 0.5 eq.) was added. The reaction mixture was slowly warmed to room temperature and stirred for 2 h before being concentrated and partitioned between dichloromethane and saturated aqueous sodium bicarbonate solution. The mixture was stirred vigorously for 15 min, before the phases were separated and the aqueous phase was extracted three times with dichloromethane and twice with a mixture of dichloromethane and 2-propanol (3:1). The combined organic phases were concentrated in vacuo to give crude trans-1-benzyl-1-aza-spiro[4.5]decan-8-ol. The alcohol was dissolved in ethanol (4 mL) containing acetic acid (15 µL) and was treated with 15 mg of palladium on charcoal (10%). The mixture was stirred under a hydrogen atmosphere (1 atm) until conversion was complete. The catalyst was filtered off and the reaction mixture was evaporated to dryness, then lyophilized from 1N HCl and water, successively, to give the crude title compound as its hydrochloride. R$_t$=0.17 min (Method 3). Detected mass: 156.2 (M+H⁺).

6-(1-Aza-spiro[4.5]dec-8-yloxy)-7-chloro-2H-iso-quinolin-1-one (Example 22)

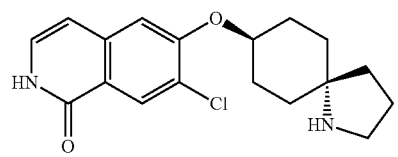 [SMILES: O=c1[nH]ccc2cc(O[C@H]3CC[C@@]4(CCCN4)CC3)c(Cl)cc12]

6-(1-Aza-spiro[4.5]dec-8-yloxy)-7-chloro-2H-isoquinolin-1-one (Example 22) was synthesized as its hydrochloride from trans-1-aza-spiro[4.5]decan-8-ol (20) and 1-benzyloxy-7-chloro-6-fluoro-isoquinoline (1) using the procedure described for Example 1. R$_t$=2.01 min (Method 2). Detected mass: 333.1 (M+H⁺).

Methods

Method 1:

| Stationary phase: | Col YMC Jsphere 33 × 2 |
|---|---|
| Gradient: | ACN + 0.05% TFA:H$_2$O + 0.05% TFA |
| | 5:95(0 min) to 95:5(2.5 min) to 95:5(3.0 min) |
| Flow: | 1 mL/min |

Method 2:

| Stationary phase: | Waters XBridge C18 |
|---|---|
| Gradient: | ACN + 0.05% TFA:H$_2$O + 0.05% TFA |
| | 5:95(0 min) to 5:95(0.3 min) to 95:5(3.5 min) to 95:5 (4 min) |
| Flow: | 1.3 mL/min |

Method 3:

| Stationary phase: | Col YMC Jsphere ODS H80 20 × 2 |
|---|---|
| Gradient: | ACN:H$_2$O + 0.05% TFA |
| | 4:96(0 min) to 95:5(2.0 min) to 95:5(2.4 min) |
| Flow: | 1 mL/min |

Method 4:

| | |
|---|---|
| Stationary phase: | Col YMC Jsphere 33 × 2.1 |
| Gradient: | ACN + 0.05% TFA:H$_2$O + 0.05% TFA<br>2:98(0 min) to 2:98(1 min) to 95:5(5 min)<br>to 95:5(6.25 min) |
| Flow: | 1 mL/min |

Method 5:

| | |
|---|---|
| Stationary phase: | Col YMC Pack Pro C18 RS 33 × 2.1 |
| Gradient: | H$_2$O + 0.1% FA:ACN + 0.1% FA<br>95:5(0 min) to 5:95(2.5 min) to 5:95(3 min) |
| Flow: | 1 mL/min |

Method 6:

| | |
|---|---|
| Stationary phase: | Column Gemini C18, 30 × 4.6 mm |
| Gradient: | H$_2$O + 0.1% FA:ACN + 0.1% FA<br>95:5(0 min) to 95:5(1 min) to 0:100(9 min) to<br>0:100(12 min) |
| Flow: | 1 mL/min |

Method 7:

| | |
|---|---|
| Stationary phase: | Column Kromasil C18, 50 × 2.1 mm, 3.5 μm |
| Gradient: | H$_2$O + NH$_4$OAc(5 mM) + 3% ACN:ACN<br>100:0(0 min) to 0:100(5.5 min) to 0:100(7 min) |
| Flow: | 0.8 mL/min |

Method 8:

| | |
|---|---|
| Stationary phase: | Column Gemini C18, 30 × 4.6 mm, 3 μm |
| Gradient: | H$_2$O + 0.1% FA:ACN + 0.1% FA<br>95:5(0 min) to 0:100(5.5 min) to 0:100(7.5 min) |
| Flow: | 1 mL/min |

Method 9:

| | |
|---|---|
| Stationary phase: | Column Acquity BEH C18, 50 × 2.1 mm, 1.7 μm |
| Gradient: | H$_2$O + 0.05% TFA:ACN + 0.035% TFA<br>98:2(0 min) to 0:100(1.6 min) to 0:100(2.1 min) to<br>98:2(3 min) |
| Flow: | 1 mL/min |

Determination of Rho Kinase Inhibition

To measure Rho-kinase inhibition, IC$_{50}$ values were determined according to the following protocol:

Active human recombinant ROCK II (N-terminal His6-tagged recombinant human ROCK-II residues 11-552) was purchased from Millipore GmbH, Schwalbach, Germany. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-hydroxyethyl)piperazine-1-ethanesulfonic acid (Hepes), Brij-35, dithiothreitol (DTT) and Pluronic F-68 were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM MgCl$_2$, 2 mM DTT, 0.02% (w/v) BSA, 0.01% Pluronic F-68 and 3% DMSO). The ROCK II enzyme was diluted to a concentration of 100 ng/ml in buffer 2 (25 mM Tris-HCl, pH 7.4, 5 mM MgCl$_2$, 2 mM DTT and 0.02% (w/v) BSA). The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 2004, 9(5), 409-416). Separation conditions were as follows: Pressure −1.3 psi, upstream voltage −1562 V, downstream voltage −500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured

| Example-No. | pIC50 |
|---|---|
| 1 | ++++++ |
| 2 | ++++++ |
| 3 | ++++++ |
| 4 | +++++ |
| 5 | ++++++ |
| 6 | +++++ |
| 7 | ++++++ |
| 8 | ++++++ |
| 9 | +++++ |
| 10 | +++++ |
| 11 | ++++++ |
| 12 | +++++ |
| 13 | +++++ |
| 14 | +++++++ |
| 15 | +++++++ |
| 16 | +++++++ |
| 17 | ++++++ |
| 18 | ++++++ |
| 19 | ++++++ |
| 20 | ++++++ |
| 21 | +++++ |
| 22 | ++++++ |

The given activity is denoted as the negative decadal logarithm of the IC$_{50}$ (pIC$_{50}$) as follows:

+: pIC$_{50}$ ≦ 3.0
++: 3.0 ≦ pIC$_{50}$ < 4.0
+++: 4.0 ≦ pIC$_{50}$ < 5.0
++++: 5.0 ≦ pIC$_{50}$ < 6.0
+++++: 6.0 ≦ pIC$_{50}$ < 7.0
++++++: 7.0 ≦ pIC$_{50}$ < 8.0
+++++++: 8.0 ≦ pIC$_{50}$

The invention claimed is:

1. A compound of the formula (I)

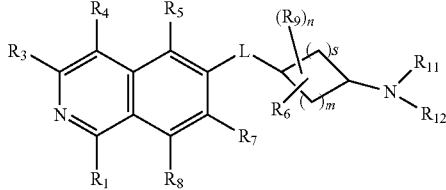

wherein
$R_1$ is H, OH or $NH_2$;
$R_3$ is H, halogen, CN, $(C_1-C_6)$alkyl, OH, $NH_2$, or NHR';
$R_4$ is H, halogen, hydroxy, CN, $(C_1-C_6)$alkyl, R', or $(C_1-C_6)$alkylene-R';
$R_5$ is H, halogen, CN, $(C_1-C_6)$alkyl, or R';
$R_7$ is H, halogen, CN, $(C_1-C_6)$alkyl, O—$(C_1-C_6)$alkyl, R', or $SO_2$—$NH_2$;
$R_8$ is H, halogen or $(C_1-C_6)$alkyl;
$R_6$ is one $(C_1-C_4)$alkylene bound to the cycloalkyl ring, in which the $(C_1-C_4)$alkylene forms a second bond to a different carbon atom of the cycloalkyl ring to form a bicyclic ring system, wherein in the bicyclic ring system one or two carbon atoms are replaced by a group independently selected from O, N—$R_{13}$, S, SO or $SO_2$;
or, if m and s are 2, m is 3 and s is 1, or m is 4 and s is 0,
$R_6$ is $CH_2$—CH—$(CH_2)_2$ which is bound with one $CH_2$ to the cycloalkyl ring and the two other $CH_2$ are bound to different carbon atoms of the cycloalkyl ring,
and, if m is 3 and s is 3,
$R_6$ are two methylene groups bound to different carbon atoms of the cycloalkyl ring, wherein the methylene groups or the $CH_2$—CH—$(CH_2)_2$ group are bound to carbon atoms of the cycloalkyl ring and form an adamantane system of the formula

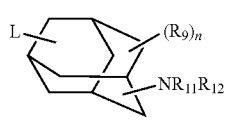

wherein L can be bound to any secondary or tertiary carbon atom,
or $R_6$ together with $R_{11}$ and the N atom form a $(C_3-C_8)$ heterocycloalkyl which is connected as a spirocyclic ring system to the cycloalkyl residue to form a residue of the formula

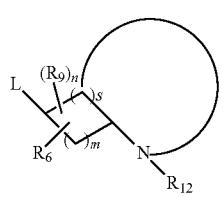

wherein the bicyclic ring system or adamantane system or the $(C_3-C_8)$heterocycloalkyl containing ring system is unsubstituted or optionally substituted by $R_9$;

$R_9$ is
R',
OH,
halogen,
$(C_1-C_6)$alkyl,
O—$(C_1-C_6)$alkyl,
$(C_1-C_6)$alkylene-R',
$(C_2-C_6)$alkenyl,
$(C_2-C_6)$alkynyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
COOH,
C(O)O—$(C_1-C_6)$alkyl,
C(O)OR'
C(O)$(C_1-C_6)$alkyl,
C(O)R',
$CONH_2$,
C(O)—NH—$(C_2-C_6)$alkenyl,
C(O)—NH—$(C_2-C_6)$alkynyl,
C(O)NH—$(C_1-C_6)$alkyl,
C(O)NHR',
C(O)—NH$(C_1-C_6)$alkylene-R',
C(O)N[$(C_1-C_6)$alkyl]R',
C(O)N[$(C_1-C_6)$alkyl]$_2$,
C(O)—$(C_1-C_6)$alkylene-R', or
C(O)O$(C_1-C_6)$alkylene-R';
$R_{11}$ and $R_{12}$ are independently of each other
H,
R',
$(C_1-C_6)$alkyl,
$(C_1-C_6)$alkylene-R',
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$,
$(C_1-C_6)$alkylene-C(O)O—$(C_1-C_6)$alkyl,
C(O)O—$(C_1-C_6)$alkyl,
C(O)OR',
C(O)$(C_1-C_6)$alkyl,
C(O)R',
C(O)NH—$(C_1-C_6)$alkyl,
C(O)NHR',
C(O)N[$(C_1-C_6)$alkyl]R',
C(O)N[$(C_1-C_6)$alkyl]$_2$,
C(O)—$(C_1-C_6)$alkylene-R',
C(O)O$(C_1-C_6)$alkylene-R', or
$R_{11}$ and $R_{12}$, together with the N-atom to which they are attached, form a $(C_3-C_8)$ heterocycloalkyl;
$R_{13}$ is H or $(C_1-C_6)$alkyl;
n is 0, 1, 2, 3 or 4;
m is 1, 2, 3 or 4;
s is 0, 1, 2, or 3;
L is O$(CH_2)_p$, S$(CH_2)_p$, S(O)$(CH_2)_p$, $SO_2(CH_2)_p$, NH$(CH_2)_p$, N$(C_1-C_6)$alkyl-$(CH_2)_p$, N$(C_3-C_6)$cycloalkyl-$(CH_2)_p$; or N[$(C_1-C_3)$alkylene-R']—$(CH_2)_p$;

p is 0, 1, 2, 3 or 4;
R' is
(C$_3$-C$_8$)cycloalkyl,
(C$_5$-C$_{10}$)heteroaryl,
(C$_3$-C$_8$)heterocycloalkyl,
(C$_6$-C$_{10}$)aryl;
wherein in residues R$_3$ to R$_{13}$ alkyl or alkylene is unsubstituted or optionally substituted one or more times by OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues R$_3$ to R$_{13}$ cycloalkyl or heterocycloalkyl is unsubstituted or optionally substituted one or more times by (C$_1$-C$_6$)alkyl, halogen, OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues R$_3$ to R$_{13}$ alkyl or alkylene is unsubstituted or optionally substituted one or more times by halogen;
wherein in residues R$_3$ to R$_{13}$ (C$_6$-C$_{10}$)aryl and (C$_5$-C$_{10}$) heteroaryl are unsubstituted or optionally substituted one or more times by a group independently selected from halogen, OH, NO$_2$, N$_3$, CN, C(O)—(C$_1$-C$_6$)alkyl, C(O)—(C$_6$-C$_{10}$)aryl, C(O)OH, C(O)O(C$_1$-C$_6$)alkyl, C(O)NH$_2$, C(O)NH(C$_1$-C$_6$)alkyl, C(O)N[(C$_1$-C$_6$) alkyl]$_2$, (C$_3$-C$_8$)cycloalkyl, (C$_1$-C$_6$)alkyl, (C$_1$-C$_6$)alkylene-NH(C$_1$-C$_6$)alkyl, (C$_1$-C$_6$)alkylene-N[(C$_1$-C$_6$) alkyl]$_2$, (C$_2$-C$_6$)alkenyl, (C$_2$-C$_6$)alkynyl, O—(C$_1$-C$_6$) alkyl, O—C(O)—(C$_1$-C$_6$)alkyl, PO$_3$H$_2$, SO$_3$H, SO$_2$—NH$_2$, SO$_2$NH(C$_1$-C$_6$)alkyl, SO$_2$N[(C$_1$-C$_6$)alkyl]$_2$, S—(C$_1$-C$_6$)alkyl; SO—(C$_1$-C$_6$)alkyl, SO$_2$—(C$_1$-C$_6$) alkyl, SO$_2$—N═CH—N[(C$_1$-C$_6$)alkyl]$_2$, SF$_5$, C(NH) (NH$_2$), NH$_2$, NH—(C$_1$-C$_6$)alkyl, N[(C$_1$-C$_6$)alkyl]$_2$, NH—C(O)—(C$_1$-C$_6$)alkyl, NH—C(O)O—(C$_1$-C$_6$) alkyl, NH—SO$_2$—(C$_1$-C$_6$)alkyl, NH—SO$_2$—(C$_6$-C$_{10}$) aryl, NH—SO$_2$—(C$_5$-C$_{10}$)heteroaryl, NH—SO$_2$—(C$_3$-C$_8$)heterocycloalkyl, N(C$_1$-C$_6$)alkyl-C(O)—(C$_1$-C$_6$) alkyl, N(C$_1$-C$_6$)alkyl-C(O)O—(C$_1$-C$_6$)alkyl, N(C$_1$-C$_6$) alkyl-C(O)—NH—(C$_1$-C$_6$)alkyl], (C$_6$-C$_{10}$)aryl, (C$_1$-C$_6$)alkylene-(C$_6$-C$_{10}$)aryl, O—(C$_6$-C$_{10}$)aryl, O—(C$_1$-C$_6$)alkylene-(C$_6$-C$_{10}$)aryl, (C$_5$-C$_{10}$)heteroaryl, (C$_3$-C$_8$) heterocycloalkyl, (C$_1$-C$_6$)alkylene-(C$_5$-C$_{10}$)heteroaryl, (C$_1$-C$_6$)alkylene-(C$_3$-C$_8$)heterocycloalkyl, O—(C$_1$-C$_6$) alkylene-(C$_5$-C$_{10}$)heteroaryl, O—(C$_1$-C$_6$)alkylene-(C$_3$-C$_8$)heterocycloalkyl,
wherein said (C$_6$-C$_{10}$)aryl, (C$_5$-C$_{10}$)heteroaryl, (C$_3$-C$_8$) heterocycloalkyl, or (C$_3$-C$_8$)cycloalkyl may be substituted one to three times by a group independently selected from halogen, OH, NO$_2$, CN, O—(C$_1$-C$_6$)alkyl, (C$_1$-C$_6$)alkyl, NH$_2$, NH(C$_1$-C$_6$)alkyl, N[(C$_1$-C$_6$)alkyl]$_2$, SO$_2$CH$_3$, C(O)OH, C(O)O—(C$_1$-C$_6$)alkyl, C(O)NH$_2$, (C$_1$-C$_6$)alkylene-O—(C$_1$-C$_6$)alkyl, (C$_1$-C$_6$)alkylene-O—(C$_6$-C$_{10}$)aryl, or O—(C$_1$-C$_6$)alkylene-(C$_6$-C$_{10}$) aryl;
or wherein (C$_6$-C$_{10}$)aryl is vicinally substituted by a O—(C$_1$-C$_4$)alkylene-O group whereby a 5-8-membered ring is formed together with the carbon atoms the oxygen atoms are attached to;
and wherein aryl substituents of (C$_6$-C$_{10}$)aryl, (C$_5$-C$_{10}$) heteroaryl, (C$_3$-C$_8$)heterocycloalkyl and (C$_3$-C$_8$)cycloalkyl groups may not be further substituted by an aryl, heteroaryl, heterocycloalkyl, or cycloalkyl containing group;
their stereoisomeric and/or tautomeric forms or a pharmaceutically acceptable salt.

2. A compound of formula (I) according to claim 1, wherein R$_1$ is H and is characterized by the formula (II)

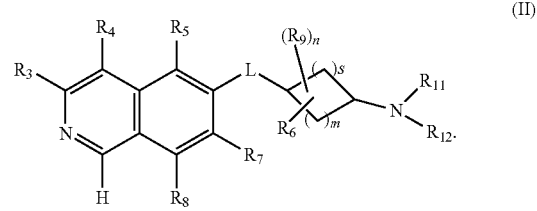

3. A compound of formula (I) according to claim 1, wherein R$_1$ is OH and is characterized by the formula (IIIa)

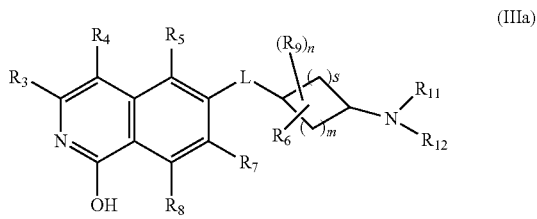

or by the formula (Mb)

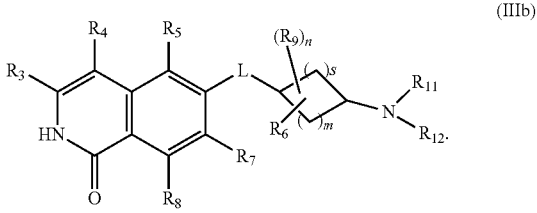

4. A compound according to claim 1, wherein R$_1$ is NH$_2$.

5. A compound according to one of claims 1 to 4, wherein R$_3$ is H, halogen, (C$_1$-C$_6$)alkyl, or NHR', wherein (C$_1$-C$_6$) alkyl and R' are unsubstituted or substituted.

6. A compound according to one of claims 1 to 4, wherein R$_3$ is H.

7. A compound according to one of claims 1 to 4, wherein R$_4$ is H, halogen, (C$_1$-C$_6$)alkyl or (C$_1$-C$_2$)-phenyl, wherein (C$_1$-C$_6$)alkyl or phenyl are unsubstituted or substituted.

8. A compound according to one of claims 1 to 4, wherein R$_4$ is H.

9. A compound according to one of claims 1 to 4, wherein R$_5$ is H, halogen, (C$_1$-C$_6$)alkyl, (C$_6$-C$_{10}$)aryl, or (C$_5$-C$_{10}$) heteroaryl, wherein (C$_1$-C$_6$)alkyl, (C$_6$-C$_{10}$)aryl, or (C$_5$-C$_{10}$) heteroaryl are unsubstituted or substituted.

10. A compound according to one of claims 1 to 4, wherein R$_5$ is H.

11. A compound according to one of claims 1 to 4, wherein R$_7$ is H, halogen, (C$_1$-C$_6$)alkyl, O—(C$_1$-C$_6$)alkyl, or R', wherein (C$_1$-C$_6$)alkyl or R' are unsubstituted or substituted.

12. A compound according to one of claims 1 to 4, wherein R$_7$ is chloro.

13. A compound according to one of claims 1 to 4, wherein R$_8$ is H.

14. A compound according to one of claims 1 to 4, wherein $R_9$ is
R',
OH,
halogen,
$(C_1-C_6)$alkyl,
$(C_1-C_8)$heteroalkyl,
$(C_1-C_6)$alkylene-R',
$(C_2-C_6)$alkenyl,
$(C_1-C_6)$alkylene-C(O)NH—R',
$(C_1-C_6)$alkylene-C(O)NH—$(C_1-C_6)$alkyl,
COOH,
CONH$_2$,
C(O)NH—$(C_1-C_6)$alkyl,
C(O)NHR',
C(O)—NH—$(C_1-C_6)$alkynyl,
C(O)—NH($C_1-C_6$)alkylene-R', or
C(O)N[$(C_1-C_6)$alkyl]$_2$;
wherein $(C_1-C_6)$alkyl, $(C_1-C_6)$alkylene or R' are unsubstituted or substituted.

15. A compound according to one of claims 1 to 4, wherein $R_9$ is OH, halogen, $(C_1-C_6)$alkyl, R', $(C_1-C_6)$alkylene-R', $(C_2-C_6)$alkenyl, COOH, CONH$_2$, C(O)NH—$(C_1-C_6)$alkyl, C(O)NHR', or C(O)N[$(C_1-C_6)$alkyl]$_2$, wherein alkyl, alkylene and R' are unsubstituted or substituted.

16. A compound according to one of claims 1 to 4, wherein $R_9$ is OH, halogen, $(C_1-C_6)$alkyl, COOH, CONH$_2$, O—CH$_3$, phenyl, $(C_1-C_2)$alkylene-phenyl, $(C_3-C_8)$cycloalkyl, wherein alkyl, phenyl or $(C_3-C_8)$cycloalkyl is unsubstituted or substituted.

17. A compound according to one of claims 1 to 4, wherein $R_9$ is allyl, methyl, ethyl, propyl, isopropyl, butyl, isobutyl, cyclopropyl, cyclobutyl, cyclopentyl, cyclopropylmethylene, isopropyloxymethylene, tetrahydrofuranyl, tetrahydropyranyl, phenyl or benzyl.

18. A compound according to one of claims 1 to 4, wherein $R_{11}$ and $R_{12}$ are independently of each other
H,
$(C_1-C_6)$alkyl,
$(C_3-C_8)$cycloalkyl,
$(C_1-C_4)$alkylene-$(C_3-C_8)$cycloalkyl,
$(C_1-C_4)$alkylene-$(C_5-C_{10})$heteroaryl,
$(C_1-C_4)$alkylene-$(C_3-C_8)$heterocycloalkyl,
$C_1-C_4)$alkylene-$(C_6-C_{10})$aryl,
$(C_1-C_6)$alkylene-O—$(C_1-C_6)$alkyl,
C(O)NH—$(C_1-C_6)$alkyl, or
$R_{11}$ and $R_{12}$, together with the N-atom to which they are attached, form a $(C_3-C_8)$ heterocycloalkyl group;
wherein $(C_1-C_6)$alkyl, $(C_3-C_8)$cycloalkyl, $(C_1-C_4)$alkylene, $C_5-C_{10})$heteroaryl, $(C_3-C_8)$heterocycloalkyl, or $(C_6-C_{10})$aryl are unsubstituted or substituted.

19. A compound according to any of claims 1 to 4, wherein $R_{11}$ is H or $(C_1-C_6)$alkyl; and
$R_{12}$ is
H,
$(C_1-C_6)$alkyl,
$(C_3-C_8)$cycloalkyl,
$(C_1-C_4)$alkylene-$(C_3-C_8)$cycloalkyl,
$(C_1-C_4)$alkylene-$(C_5-C_{10})$heteroaryl,
$(C_1-C_4)$alkylene-$(C_3-C_8)$heterocycloalkyl,
$(C_1-C_4)$alkylene-$(C_6-C_{10})$aryl, or
$(C_1-C_4)$alkylene-O—$(C_1-C_6)$alkyl,
wherein $(C_1-C_6)$alkyl, $(C_3-C_8)$cycloalkyl, $(C_1-C_4)$alkylene, $(C_5-C_{10})$heteroaryl, $(C_3-C_8)$heterocycloalkyl, or $(C_6-C_{10})$aryl are unsubstituted or substituted.

20. A compound according to any of claims 1 to 4, wherein
$R_{11}$ is H and
$R_{12}$ is H, $(C_1-C_6)$alkyl or $(C_3-C_8)$cycloalkyl,
wherein $(C_1-C_6)$alkyl or $(C_3-C_8)$cycloalkyl are unsubstituted or substituted.

21. A compound according to any of claims 1 to 4, wherein $R_{11}$ and $R_{12}$ are H.

22. A compound according to one of claims 1 to 4, wherein the bicyclus formed with $R_6$ is selected from the group

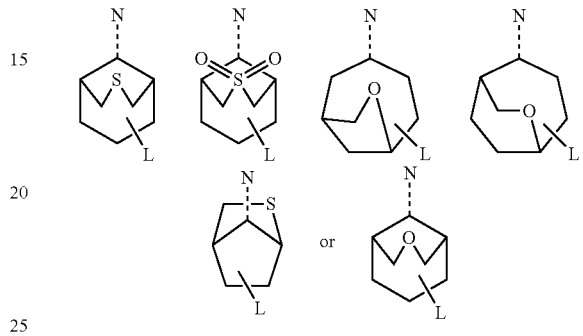

which is unsubstituted or optionally substituted by $R_9$.

23. A compound according to one of claims 1 to 4, wherein the adamantane formed with $R_6$ is selected from

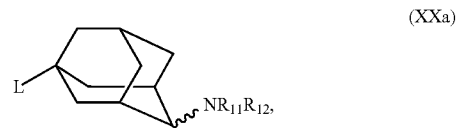

(XXa)

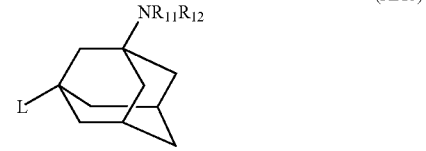

(XXb)

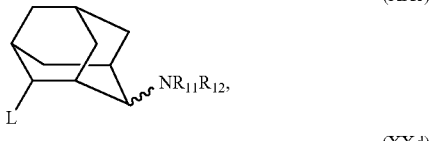

(XXc)

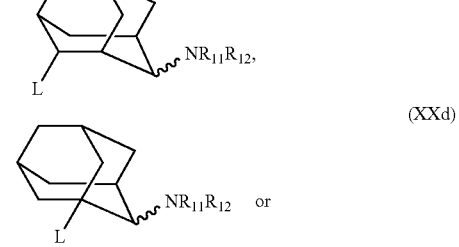

(XXd)

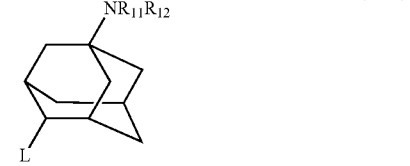

(XXe)

which is unsubstituted or optionally substituted by residues $R_9$.

24. A compound according to one of claims 1 to 4, wherein $R_6$ together with $R_{11}$ and the N atom form a $(C_3-C_8)$hetero cycloalkyl which is connected as a spirocyclic system to the cycloalkyl residue to give a residue of the formula

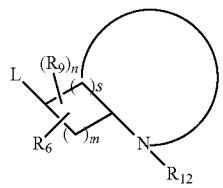

(XXI)

wherein the $(C_3-C_8)$heterocycloalkyl containing ring system is unsubstituted or optionally substituted by $R_9$.

25. A compound according to one of claims 1 to 4, wherein m is 2 and s is 2.

26. A compound according to one of claims 1 to 4 wherein m is 3 and s is 1.

27. A compound according to one of claims 1 to 4, wherein n is 0.

28. A compound according to one of claims 1 to 4, wherein L is $S(CH_2)_p$, $S(O)(CH_2)_p$, or $SO_2(CH_2)_p$.

29. A compound according to one of claims 1 to 4, wherein L is $NH(CH_2)_p$ or $N(C_1-C_6)alkyl)-(CH_2)_p$.

30. A compound according to one of claims 1 to 4, wherein L is $O(CH_2)_p$.

31. A compound according to one of claims 1 to 4, wherein p is 0.

32. A compound according to claim 1 selected from the group consisting of
    6-(4-Amino-adamantan-1-yloxy)-7-chloro-2H-isoquinolin-1-one,
    6-(4-Allyl-4-amino-adamantan-1-yloxy)-7-chloro-2H-isoquinolin-1-one,
    6-(4-Amino-4-propyl-adamantan-1-yloxy)-7-chloro-2H-isoquinolin-1-one,
    6-(4-Amino-4-methyl-adamantan-1-yloxy)-7-chloro-2H-isoquinolin-1-one,
    6-(4-Amino-4-phenyl-adamantan-1-yloxy)-7-chloro-2H-isoquinolin-1-one,
    6-(4-Amino-4-cyclopropyl-adamantan-1-yloxy)-7-chloro-2,4-isoquinolin-1-one,
    6-(4-Benzylamino-adamantan-1-yloxy)-7-chloro-2H-isoquinolin-1-one,
    6-(3-Amino-adamantan-1-yloxy)-7-chloro-2,4-isoquinolin-1-one,
    6-(5-Amino-adamantan-2-yloxy)-7-chloro-2H-isoquinolin-1-one,
    6-(5-Amino-adamantan-2-yloxy)-7-methyl-2H-isoquinolin-1-one,
    6-{[(7-amino-3-oxabicyclo[3.3.1]non-9-yl]oxy}-7-chloroisoquinolin-1(2H)-one,
    6-{[(7-amino-3-thiabicyclo[3.3.1]non-9-yl]oxy}-7-chloroisoquinolin-1(2H)-one,
    6-{[(7-amino-3-(dioxo-thia)bicyclo[3.3.1]non-9-yl]oxy}-7-chloroisoquinolin-1(2H)-one, 3,3-dioxide, or
    6-(1-Aza-spino[4.5]dec-8-yloxy)-7-chloro-2H-isoquinolin-1-one,
    their stereoisomeric and/or tautomeric forms or a pharmaceutically acceptable salt.

33. A compound according to claim 1 selected from the group consisting of
    cis-6-(5-Amino-adamantan-2-yloxy)-7-chloro-2H-isoquinolin-1-one,
    trans-6-(5-Amino-adamantan-2-yloxy)-7-chloro-2H-isoquinolin-1-one,
    6-{[(7-Endo,9-anti)-7-amino-3-oxabicyclo[3.3.1]non-9-yl]oxy}-7-chloroisoquinolin-1(2H)-one,
    6-{[(7-endo,9-syn)-7-amino-3-oxabicyclo[3.3.1]non-9-yl]oxy}-7-chloroisoquinolin-1(2H)-one,
    6-{[(7-Endo,9-anti)-7-amino-3-thiabicyclo[3.3.1]non-9-yl]oxy}-7-chloroisoquinolin-1(2H)-one,
    6-{[(7-endo,9-syn)-7-amino-3-thiabicyclo[3.3.1]non-9-yl]oxy}-7-chloroisoquinolin-1(2H)-one, and
    6-{[(7-Endo,9-anti)-7-amino-3-(dioxo-thia)bicyclo[3.3.1]non-9-yl]oxy}-7-chloroisoquinolin-1(2H)-one, 3,3-dioxide,
    their stereoisomeric and/or tautomeric forms or a pharmaceutically acceptable salt.

34. A compound of formula (I) and/or its pharmaceutically acceptable salt according to one of claims 1 to 4 for use as a medicament.

35. A method for the treatment and/or prevention of hypertension, pulmonary hypertension, ocular hypertension, retinopathy, glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy, infection of digestive tracts with bacteria, sepsis or cancer development and progression by administering a therapeutically effective amount of a compound of claim 1 or a pharmaceutically acceptable salt thereof to a patient in need of said treatment.

36. A method for the treatment and/or prevention of hypertension, pulmonary hypertension, fibroid liver, liver failure, nephropathy, renal failure, chronic obstructive pulmonary disease (COPD), cerebral vasospasm, pain, spinal cord injury, erectile dysfunction, blood vessel restenosis, or cancer development and progression by administering a therapeutically effective amount of a compound of claim 1 or a pharmaceutically acceptable salt thereof to a patient in need of said treatment.

37. A pharmaceutical composition comprising an effective amount of at least one compound of formula (I) and/or a pharmacologically acceptable salt thereof according to one of claims 1 to 4, pharmaceutically tolerated excipients and carriers and, where appropriate, further additives and/or other active ingredients.

* * * * *

UNITED STATES PATENT AND TRADEMARK OFFICE
CERTIFICATE OF CORRECTION

PATENT NO. : 8,524,737 B2  Page 1 of 1
APPLICATION NO. : 13/000202
DATED : September 3, 2013
INVENTOR(S) : Plettenburg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this

Fifteenth Day of September, 2015

Michelle K. Lee
*Director of the United States Patent and Trademark Office*